(12) United States Patent
Kang et al.

(10) Patent No.: US 7,867,716 B2
(45) Date of Patent: Jan. 11, 2011

(54) HIGH TEMPERATURE ION CHANNELS AND PORES

(75) Inventors: Xiaofeng Kang, College Station, TX (US); Li Qun Gu, Columbus, MO (US); Stephen Cheley, Okemos, MI (US); Hagan Bayley, Oxford (GB)

(73) Assignee: The Texas A&M University System, College Station, TX (US)

( * ) Notice: Subject to any disclaimer, the term of this patent is extended or adjusted under 35 U.S.C. 154(b) by 845 days.

(21) Appl. No.: 11/314,174

(22) Filed: Dec. 21, 2005

(65) Prior Publication Data
US 2008/0101988 A1    May 1, 2008

Related U.S. Application Data

(60) Provisional application No. 60/637,919, filed on Dec. 21, 2004.

(51) Int. Cl.
*G01N 33/53* (2006.01)
(52) U.S. Cl. ............... 435/7.1; 435/7.2; 422/82.01; 422/82.02; 204/435
(58) Field of Classification Search ............ 204/435; 422/82.2; 435/7.1
See application file for complete search history.

(56) References Cited

U.S. PATENT DOCUMENTS 6,426,231 B1    7/2002    Bayley et al.
6,927,070 B1    8/2005    Bayley et al.
2003/0029722 A1*    2/2003    Erdosy et al. ............... 204/435
2003/0215881 A1    11/2003    Bayley et al.

OTHER PUBLICATIONS

Pastorzia-Gallego et al., Urea denaturation of a-hemolysin pore inserted in planar lipid bilayer detected by single nanopore recording: loss of structural asymmetry, Jun. 26, 2007, FEBS Letters 581, 3371-3376.*
Bayley, H., L. Jayasinghe, "Functional Engineered Channels and Pores," Mol. Membrane Biol. 2004, 21, 209-220.
Beckstein, et al. "Liquid-vapor oscillations of water in hydrophobic nanopores" Proc.Natl.Acad.Sci. USA 2003, 100, 7063-7068.
Braha, et al. "Designed protein pores as components for biosensors," Chem.Biol. 1997, 4, 497-505.

(Continued)

*Primary Examiner*—Tony G Soohoo
*Assistant Examiner*—Robert Eom
(74) *Attorney, Agent, or Firm*—Chalker Flores, LLP; Chainey P. Singleton; Edwin S. Flores

(57) ABSTRACT

The present invention includes an apparatus, system and method for stochastic sensing of an analyte to a protein pore. The protein pore may be an engineer protein pore, such as an ion channel at temperatures above 55° C. and even as high as near 100° C. The analyte may be any reactive analyte, including chemical weapons, environmental toxins and pharmaceuticals. The analyte covalently bonds to the sensor element to produce a detectable electrical current signal. Possible signals include change in electrical current. Detection of the signal allows identification of the analyte and determination of its concentration in a sample solution. Multiple analytes present in the same solution may also be detected.

12 Claims, 11 Drawing Sheets

OTHER PUBLICATIONS

Caterina, et al., "Acapsaicin-receptor homologue with a high threshold for noxious heat," Nature 1999, 398, 436-441.

Conlan, et al "Biochemical and Biophysical Characterization of OmpG: A Monomeric Porin," Biochemistry 2000, 39, 11845-11854.

Conlan, et al. "Folding of a Monomeric Porin, OmpG, in Detergent Solution," Biochemistry 2003, 42, 9453-9465.

Gu, et al. Stochastic sensing of organic analytes by a pore-forming protein containing amolecular adapter, Nature 1999, 398, 686-690.

Gu, et al., "Prolonged Residence Time of a Noncovalent Molecular Adapter, β-Cyclodextrin, within the Lumen of Mutant α-Hemolysin Pores," J.Gen.Physiol. 2001, 118, 481-494.

Haltia, T., E. Faeire, "Forces and factors that contribute to the structural stability of membrane proteins," Biochem. Biophys. Acta 1995, 1241, 295-322.

Howorka, et al., "Sequence-specific detection of individual DNA strands using engineered nanopores," Nature Biotechnology 2001, 19, 636-639.

Howorka, et al., "Kinetics of duplex formation for individual DNA strands within a single protein nanopore," Proc.Natl. Acad. Sci. USA 2001, 98, 12996-13001.

Liu, et al., "Thermodynamics of Heat Activation of Single Capsaicin Ion Channels VR1," Biophys.J. 2003, 85, 2988-3006.

Meller, et al. "Rapid nanopore discrimination between single polynucleotide molecules," Proc. Natl. Acad. Sci. USA 2000, 97, 1079-1084.

Miles, et al., "The Staphylococcal Leukocidin Bicomponent Toxin Forms Large Ionic Channels," Protein Sci. 2002, 11, 894-902.

Miles, et al. "Subunit composition of a bicomponent toxin: Staphylococcal leukocidin forms an octameric transmembrane pore," Biochemistry 2001, 40, 8514-8522.

Olson, et al. "Crystal structure of Staphylococcal LukF delineates conformational changes accompanying formation of a transmembrane channel," Nature Struct. Biol. 1999, 6, 134-140.

Pedelacq, et al. "The structure of a Staphylococcus aureus leucocidin component (LukF-PV) reveals the fold of the water-soluble species of a family of transmembrane pore-forming toxins," Structure 1999, 7, 277-288.

Pusch, et al., "Temperature Dependence of Fast and Slow Gating Relaxations of ClC-0 Chloride Channels," J. Gen. Physiol. 1997, 109, 105-116.

Rothchild, L. J., R. L. Mancinelli, "Life in extreme environments," Nature 2001, 409, 1092-1101.

Sauer, et al. "Stability and Function of Interdomain Linker Variants of Glucoamylase 1 from Aspergillus niger," Biochemistry 2001, 40, 9336-9346.

Sigurskjold, et al. "Thermodynamics of ligand binding to the starch-binding domain of glucoamylase from Aspergillus niger," Eur.J. Biochem. 1994, 225, 133-141.

Sigurskjold, et al. "Thermodynamics of Binding of Heterobidentate Ligands Consisting of Spacer-Connected Acarbose and â-Cyclodextrin to the Catalytic and Starch-Binding Domains of Glucoamylase from Aspergillus niger Shows That the Catalytic and starch-Binding Sites Are in Close Proximity in Space," Biochemistry 1998, 37, 10446-10452.

Song, et al "Structure of Staphylococcal #-Hemolysin, a Heptameric Transmembrane Pore," Science 1996, 274, 1859-1865.

Wang, J., M.A. El-Sayed, "The Effect of Protein Conformation Change from all to al on the Bacteriorhodopsin Photocycle," Biophys. J. 2000, 78, 2031-2036.

Supplementary European Search Report for EP 05858727.0 dated Apr. 15, 2009.

Baker, M. D., et al., "The pH dependence of late sodium current in large sensory neuron," Neuroscience (1999), 92:1119-1130.

Belmonte, G., et al., "Pore formation by Staphyloccocus aureus alpha-toxin in lupid bilayers. Dependence upon temperature and toxin concentration," European Biophysics Journal (1987), 14:349-358.

Fujiwara-Hirashima, C., et al., "A voltage-dependent chloride channel from Tetrahymena ciliary membrane incorporated into planar lipid bilayers," Biochimica et Biophysica Acta (1996), 1280:207-216.

Howorka, S., et al., "Kinetics of duplex formation for individual DNA strands within a single protein nanopore," PNAS (2001), 98:12996-13001.

Kang, X., et al., "High Temperature protein nanopore," Abstracts of Papers American Chemical Society (2003), 226:1-2.

Kang, X., et al., "Single protein pores containing molecular adapters at high temperature," Angewandte Chemie—International Edition (2005), 44:1495-1499.

Maier, E., et al., "Identification of the outer membrane porin of Thermus thermophilus HB8: The channel-forming complex has an unusually high molecular mass and an extremely large single-channel conductance," Journal of Bacteriology (2001), 183:800-803.

Meller, A., et al., "Rapid nanopore discrimination between single polynucleotide molecules," PNAS (2000), 97:1079-1084.

Oosawa, Y., et al., "A cation channel for K+ and Ca2+ from Tetrahymena cilia in planar lipid bilayers," Cell Structure and Function (1988), 13:51-60.

* cited by examiner

HIGH TEMPERATURE ION CHANNELS AND PORES

This application claims priority to U.S. Provisional Patent Application Ser. No. 60/637,919, filed Dec. 21, 2004, the entire contents of which are incorporated herein by reference.

STATEMENT OF GOVERNMENT INTEREST

The present invention was conceived or reduced to practice using funds provided by DARPA, the DoD Tri-Service Technology Program, DOE, NASA, NIH and ONR. The US government has certain rights in the invention.

TECHNICAL FIELD OF THE INVENTION

The present invention relates in general to the field of ion channels, and more particularly, to protein pores and ion channels that are functional and stable at temperatures above 55° C.

BACKGROUND OF THE INVENTION

Without limiting the scope of the invention, its background is described in connection with stochastic sensing based on the detection of individual binding events between analyte molecules and a single sensor element. Upon binding, a property of the sensor element is altered. This property or the effects of the changed property are measured.

In a simple example, the sensor element is a protein that is altered when it binds another molecule. The binding molecule to be detected is referred to as the analyte. The alteration of the sensor element that occurs upon binding is measured either directly or indirectly. In simple systems the alteration produces a simple signal, such as a difference in electrical current, force or fluorescence. Measurements of the signal indicate whether the analyte is bound and how long it remains bound. The frequency of occurrence of binding events is determined by the concentration of the analyte. The nature of the binding event is determined by the binding properties of the analyte, which determine, for example, the magnitude and duration of the resulting signal. Thus, a single sensor element to which multiple analytes may bind either directly may be used to determine which of those analytes are in a solution and the concentration of each particular analyte.

Protein pores are being developed for use in stochastic sensing.[1] For several applications, the pores must be stable at high temperatures. The structures of many integral membrane proteins remain intact at high temperatures[2] and the existence of extremophiles implies that membrane proteins function at 100° C. and beyond.[3] However, few measurements of membrane protein activity have been made at temperatures above ~55° C., and none have been made for ion channels and pores.

The photocycle of bacteriorhodopsin, for example, has been examined at temperatures up to 85° C.[4] The activity is compromised above 60° C. because the chromophore, a transretinal Schiff's base, isomerizes to the 13-cis form. Transmembrane proton pumping was not measured directly in these experiments. Macroscopic current recordings with valinomycin (a macro cyclic antibiotic) have been carried out at up to 80° C. in bilayers comprising lipids from a hyperthermophile, *Caldariella acidophila*.[5]

In the case of proteinaceous channels and pores, activity has been measured at up to ~55° C. For example, multichannel recordings of vanilloid receptors (temperature-sensitive cation channels) have been made after expression in *Xenopus* oocytes, and several subtypes of the receptor remain active at 55° C.[6] Recently, single channel recordings of the vanilloid receptor VR1 have been made at up to 55° C.[7] The transmembrane domains of these proteins are presumably largely α-helical.

Stochastic sensing may be accomplished with various sensing elements, using various modes of detection. One simple model uses an ion channel protein pore embedded in a membrane between a cis chamber and a trans chamber. When the pore is fully open a large ion flux occurs (e.g., $10^8$ ions/s) which constitutes an electrical current that may be monitored by single channel recording. When an analyte binds to the pore, ion flux is altered, usually by decreasing the flow of ions. This generates a current trace that shows conduction over time.

One particular pore that has been used in stochastic sensing is *Staphlococcus* alpha hemolysin (αHL), which is actually an exotoxin secreted by *Staphylococcus aureus*. The monomeric 293 amino acid polypeptide can self-assemble on lipid bilayers, such as membranes, to form a heptameric pore. Alternatively, pre-formed pores may be inserted into a lipid bilayer. The pore is a mushroom-shaped structure in which the lower half of the stem forms a transmembrane channel. The interior of the pore is referred to as the "lumen" and may be accessible from outside the pore. By convention, when the pore is situated in a membrane, the side of the membrane on which the top of the mushroom shape is located is designated as the "cis" side of the membrane. The side of the membrane to which the stem portion leads is designated the "trans" side of the membrane. The pore essentially forms a hole in the membrane through which ions will flow if an electric potential is generated between the two chambers.

Measurements on the pore-forming toxin, α-hemolysin, one of the proteins examined in the present application, have been made previously at up to 50° C.[8-10] This protein largely includes β structures. Indeed, all three of the proteins examined here contain β barrels, which are formed from either a single subunit, OmpG; seven subunits, α-hemolysin (αHL); or eight subunits, leukocidin (Luk). OmpG is a 280-residue polypeptide that forms a β barrel of, most likely, 16 antiparallel strands. Unlike most porins, which are trimeric, OmpG functions as a monomer.[11] The homoheptameric pore formed by αHL is a mushroom-shaped structure.[12] The stem of the mushroom is a 14-stranded transmembrane β barrel with two strands contributed by each subunit. The stem is capped by a large hollow extracellular domain. The Luk pore contains two types of subunits, F and S, which are related in sequence and structure to αHL.[13,14] The pore is a heterooctamer containing four F and four S subunits.[15] Despite the presence of only one additional subunit, the unitary conductance of the Luk pore is more than three times that of the αHL pore.[16]

SUMMARY OF THE INVENTION

The present invention relates to protein pores and ion channels that are functional and sable at higher temperatures and may be used for stochastic sensing. In specific embodiments, the pores and ion channels are functional and stable for stochastic sensing at temperatures above 55° C. The present invention includes the use of multiple pores and channels may are functional and stable for stochastic sensing at temperatures approaching 100° C. Pores and channels used for stochastic sensing in certain embodiments of the invention include αHL, Omp G and Luk. In a particular embodiment, the present invention includes βCD used in combination with αHL.

The apparatus, systems and methods of the present invention will find particular uses for the detection and characterization of single molecules as they affect a single protein pore. For example, the single-channel or pore for use at high temperatures of the present invention may be used for the study, characterization and manipulation of extremophiles and even for the study of single-molecule covalent chemistry.

The present invention may facilitate any stochastic sensing at temperatures above 55° C. One advantage of some embodiments as compared to antibiotic and other analyte sensing systems operable at higher temperatures lies in the ability to engineer easily alternative protein pores. Additionally, as compared to older protein pore stochastic sensing systems, embodiments of the present invention may be more useful for nanotechnology because of the capacity to operate at higher temperatures. Embodiments of the present invention may also be particularly useful in technologies in which DNA is measures, such as direct DNA sequencing. For a single-stranded DNA to enter a protein pore, it must be denatured, which requires a temperature above 55° C. in almost all instances.

More particularly, the present invention includes a system for sensing one or more analytes in a solution by using a sensing device separated into first and second chambers separated by a divider having one or more protein pores operably disposed in or about the divider. A detection system operable to detect current between the first and second chambers is provided such that a solution with the one or more analytes that is capable of bonding to the protein pore, wherein bonding of the reactive analyte to the one or more protein pores produces a change in current between the first and second chambers detectable by the current detection system and is operable at a temperature at or above 55° C.

The protein pore may be an engineered protein pore, such as a αHL, Omp G and Luk protein pore, fusion proteins and combinations thereof. For example, the analyte may be disposed in an ionic solution that is a pH buffered KCl solution. The analyte mae be, e.g., an environmental toxin, a chemical weapon, a drug, a steroid, a pharmaceutical, an arsenical or combinations thereof. Often, the analyte will be disposed in an ionic solution that includes one or more species of chemically distinct analytes capable of bonding with the protein pore. The detection system may be any that is capable of detecting conductance or other ionic variations, e.g., those capable of stochastic sensing. When detecting stochastically, the change in current may be a change in the magnitude of the current.

The system may also be capable of detecting at least a second analyte, wherein the second analyte bonds to the protein pore and a detection system operable to detect a signal produced by covalent bonding of an analyte to the protein pore, wherein the detection system is capable of distinctly detecting the signals produced by bonding of at least the first and second analytes to the protein pore. Furthermore, the one or more different protein pores that have been functionalized to detect different analytes. In certain embodiments, the system is operable at a temperature at or near, 60, 70, 80, 90 or even 100° C.

The present invention also includes methods for sensing one or more analytes in a solution by disposing operably a protein pore in a divider between a first and a second chamber and detecting a current between the first and a second chambers with a current detector when the protein pores are exposed to a solution suspected of having the one or more analytes at a temperature at or above 55° C., wherein the one or more analytes produces a change in current between the first and a second chambers detectable by the current detector.

The invention also includes an apparatus for the detection of one or more analytes that includes a first and a second chamber separated by a divider that has one or more protein pores operably disposed in or about the divider. A detector is connected operably to detect current between the first and second chambers at a temperature of above 55° C.; and a solution suspected of having one or more analytes capable of bonding to the protein pore is contacted with the detectors, wherein the binding of the reactive analyte in a solution to the protein pore at the divider produces a detectable change in current between the first and second chambers detectable by the current detection system.

The temperature of the first and/or second chambers may be controlled by a Peltier device or other heating element. Often, the divider may be made from a solid or flexible materials that may also be coated a with a non-reactive coating, such as TEFLON® and derivatives thereof. The first, second or both chambers may be made from any of a wide variety or materials, e.g., glass, quartz, silicon, coated stainless steel, nylon, polyethylene, polystyrene, polypropylene and combinations thereof. Detectors for use with the present invention may be customized for the level of detection, e.g., quantitative and/or qualitative and may even include semiconductors and/or pads, e.g., a detector that has noble metal sensors in communication with the first and second chambers. The divider includes an opening that may have a lipid bilayer into which the one or more protein pores are disposed. Non-limiting examples of protein pores are those that are functional at temperature at or above 56° C., e.g., αHL, Omp G and Luk, derivatives, mutants and fusion proteins that include combinations of these protein pores. The protein pores may include one or more protein pores selected from αHL, Omp G and Luk and combinations thereof and these protein pores may be further functionalized with one or more functional group that bind specifically to a specific target at temperatures above 55° C., 56° C. and even 60, 70, 80, 90 or even 100° C.

BRIEF DESCRIPTION OF THE DRAWINGS

For a more complete understanding of the features and advantages of the present invention, reference is now made to the detailed description of the invention along with the accompanying figures and in which:

FIG. 5A shows the variation of bilayer capacitance (C) with temperature (T). The capacitance was determined by applying a triangular wave of 100 mV$_{p-p}$ at 25 Hz and monitoring the current response. FIG. 5B presents a recording of the current passed by multiple αHL pores as a function of temperature. A representative current trace at −40 mV is shown. The numbers on the trace are the numbers of channels present at a given time, estimated from the observed number of current steps. The buffer in both chambers was 10 mM Na phosphate, pH 7.5, containing 1 M NaCl.

FIG. 7A shows ln k$_{on}$ versus 1/T. FIG. 7B shows ln k$_{off}$ versus 1/T. FIG. 7C shows ln K$_f$ versus 1/T. FIGS. 7A, 7B and 7C each show the result from a typical experiment (from four total). k$_{on}$, k$_{off}$ and K$_f$ are marked on the y-axes as dimensionless, which they are, strictly speaking. This arises because dimensionless activity values are replaced by molar concentrations herein, as is common in the art. Further, the y-axes in FIGS. 7A and 7B should strictly be ln k/φ, where φ is a frequency factor of dimension s$^{-1}$. In practice, and herein, ln φ is usually separated and appears in the y intercept.

FIG. 8A illustrates representative single channel current traces obtained at various temperatures. Broken line, zero current; level 1, current through open WT$_1$(M113N)$_6$ pore; level 2, current through WT$_1$(M113N)$_6$·βCD. The buffer in both chambers was 10 mM Na phosphate, pH 7.5, containing 1 M NaCl. The applied potential was −40 mV. FIG. 8B illustrates ln K$_f$ versus 1/T in a typical plot.

FIG. 9A shows ln k$_{on}$ for adamantane-1 carboxylic acid versus 1/T. FIG. 9B shows ln k$_{off}$ versus 1/T. FIG. 9C shows ln K$_f$ versus 1/T. In FIGS. 9A, 9B and 9C the error bars represent: ±SD (n=3). k$_{on}$, k$_{off}$ and K$_f$ are marked on the y-axes as dimensionless as explained for FIG. 7.

DETAILED DESCRIPTION OF THE INVENTION

Figure 1A:
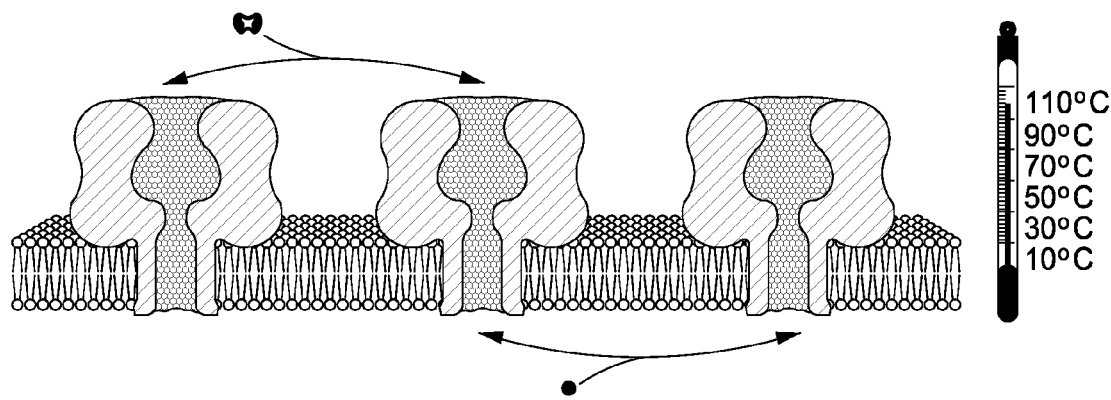
FIG. 1A presents a schematic representation of one of the pores used in embodiments of the present invention. Three states of the α-hemolysin (αHL) pore in a lipid bilayer are shown. At high temperatures, the unoccupied pore retains its ability to bind molecular adapters such as β-cyclodextrin (βCD, center), which can in turn bind guest molecules (right).

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention relates to protein pores that are stable at high temperatures. The pores may be used to measure the properties of various analytes. In specific embodiments, the protein pores are active at temperature above 55° C. Pores may remain active up to temperatures near 100° C. The pore functions as a sensor element and may be an isolated or engineered protein pore, such as an ion channel.

Additionally, a variety of signals and bonding detection procedures may be used. Signals include conductance, fluorescence, force and any other effects of analyte binding to the chosen sensor element. These signals may be detected using electrical and optical measurements, force measurements, chemical techniques and any combination of the above.

As used herein, the term "analyte" refers to reactive chemicals or agents that covalently or non-covalently bond to the sensor element (e.g., the pore and divider) under stochastic sensing conditions. Covalent bonds may be reversible or irreversible. The analytes may be any type of chemical including toxins, environmental indicators, chemical process products or by-products and contaminants. Chemical warfare agents that may be detected using the present invention include, e.g., arsenicals, organophosphates, mustard gasses, etc. Other chemicals that may be detected include those in, e.g., foodstuffs, such as onion and garlic. Other chemicals that may be detected include those in, e.g. soil samples to detected, e.g., pesticides such as organophosphates. Analytes may also include naturally occurring environmental toxins or reactive pharmaceuticals. Many physiological molecules such as nitric oxide, endo and exo peroxides are extremely reactive messengers and may also be analytes that are detectable using the present invention.

Analytes may bond to the sensor element alone or in combination with a second molecule, such as a host or adaptor molecule. The analyte may bond to the second molecule, which then bonds to the sensor element. Alternatively, the second molecule may simply affect the reaction kinetics of analyte bonding. If used to affect the reaction kinetics, the second molecule may be used to slow down or speed up rate of bonding or duration of the bound state to facilitate detection of the identity, concentration, or other properties of the analyte. The second molecule may also exert an effect on analyte bonding reaction kinetics by interacting with the analyte while not bound to the sensor element.

Other chemicals that act upon the bound analyte or are otherwise affected by the analyte/sensor element combination may also be added to the sensing system to augment sensing. For instance, an analyte bound to an αHL pore that causes a change in ion flux, but is not easily distinguishable from another analyte by current trace may be distinguished by introduction of a chemical that cleaves one of the indistinguishable analytes, but not the other. Additionally, added chemicals may be used to further explore the chemical identity properties of the analyte using sensing methods other than the original sensor element.

Previous inventions have discussed the usefulness of protein pores and ion channels in analyte sensing. For example, U.S. Pat. No. 6,426,231, U.S. Published Application No. 2003/0215881 and U.S. application Ser. No. 10/180,792, all relate to stochastic sensing of one or more analytes using a protein pore or ion channel, such as the αHL pore, relevant portions of each of which are incorporated herein by reference. The assay systems disclosed in these references may be used to perform stochastic sensing or other assays.

The stochastic sensing methodologies of the present invention may use a variety of physical arrangements and be provided in numerous configurations. For example, systems using protein pore arrangements may have the pore embedded in a membrane, located between separate cis and trans chambers. It may be recommended to place the analyte in either the cis or the trans chamber exclusively, or the system may be readily functional regardless of the chamber in which the analyte is placed. The same is true for chamber placement of any adapter or chemical reagent for breaking of irreversible bonds. In most systems the chemical reagent will be placed in one chamber and the analyte in the other chamber.

It is also possible to prepare a sensing system in which portions of the system are introduced in a time-dependent manner or varied over time. In other embodiments the sample to be tested for analyte may be discharged and replaced over time. This may result from periodic introduction of new samples or by flowing a continuous stream of sample through the sensor. For example, a sensor system to detect the presence of a reactive chemical in industrial effluent may contain a chamber through which a small diverted stream of effluent flows. In such examples it may be necessary to regulate flow so that the sample remains in proximity with the sensor element for a sufficient amount of time to statistically allow detection of a particular analyte at or above a selected concentration.

The systems and methodologies of the present invention may be used in sensors for detection of various reactive molecules. These sensors may be fixed or portable and they may be designed for single-use applications or any number of multiple uses. Remote application sensors that may be placed or dropped in a target location and then transmit sensor information may also be used. Solutions or other chemicals for use in the sensors may be supplied with the sensors in a kit, or supplied independently for use with the sensors.

Generally, the materials from which the chambers, sensors, pads, input/output (I/O) sensors, etc., will depend on the nature of the solution or gas into which the analyte is provided or disposed. Non-limiting examples of materials from which the chambers and sensors or pads may be made include, e.g., glass, quartz, silicon, nylon, polyethylene, polypropylene, stainless steel, titanium, aluminum and the like. Generally, the chambers may be made from non-reactive materials, however, materials may be coated with, e.g., TEFLON® and/or the material may be anodized to reduce its reactivity. Depending on the nature of the use (qualitative versus quantitative) of the apparatus and the location of use (laboratory versus field) the materials may be selected to optimize the nature of the signal obtained and the robustness of the system (e.g., military field use).

While not necessary, the analyst may be disposed in a solution that may be aqueous, non-aqueous or that may be or may include agents that are both hydrophobic and hydrophilic, as are well known to the skilled artisan. For example, hydrophobic agents may be made less hydrophobic by the addition of bivalent molecules that help to increase the analyte's solubility in water, e.g., fatty acids.

In certain embodiments of the present invention, an αHL protein pore may be embedded in a membrane that separates a cis chamber from a trans chamber. The membrane may be made from any of the materials outlined hereinabove, however, in certain applications the materials for the membrane may be a flexible membrane, e.g., silicone and may even be coated with a non-reactive material. The interaction of the analyte, such as an organoarsenic compound, with the αHL, blocks the of ions through the pore. This change in ion concentration in the cis and trans chambers modulates a current flow through a conductor connecting the two chambers. Measurement of this current to produce a current trace allows determination of when the analyte bonds with the αHL and when it becomes unbound.

When using the αHL pore, most analytes may be added to either the cis or the trans side, although analytes can more readily reach the pore from the trans side. The same is true for many adapters or chemical reagents for reversal of irreversible bonds. In certain embodiments of the present invention, single-molecule activity measurements have been performed using three proteinaceous membrane pores at temperatures close to 100° C. Specifically, one of the pores can bind a molecular adapter, β-cyclodextrin (βCD), at elevated temperatures. The complex retains the ability to recognize small molecules, permitting stochastic sensing in aqueous solution under extreme conditions (See FIG. 1A).

Figure 5A:
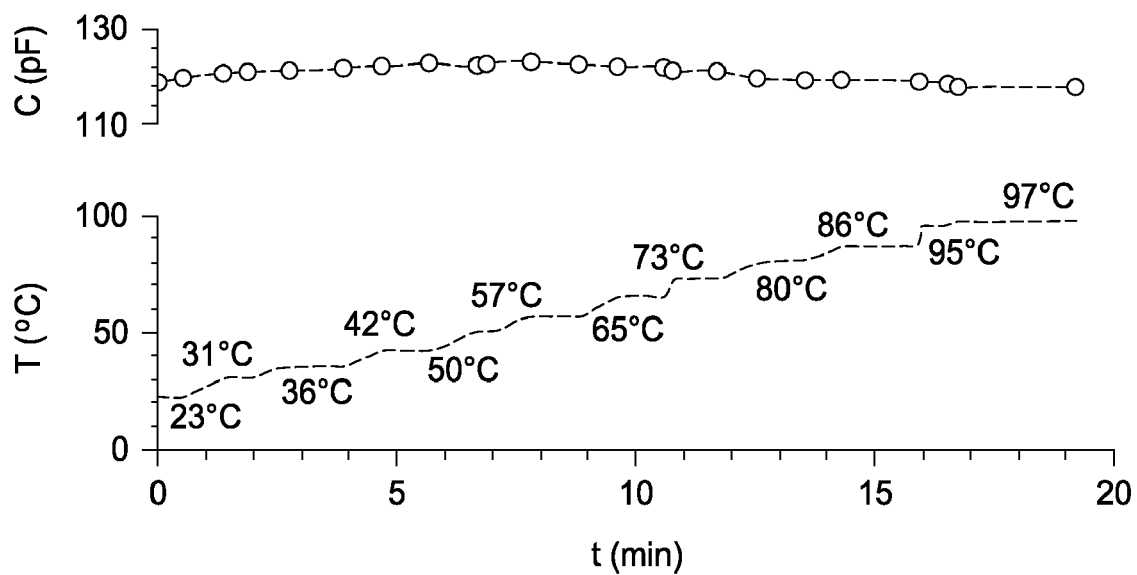
FIGS. 5A and 5B are graphs that illustrate bilayer capacitance and multichannel currents at elevated temperatures.

Lipid bilayers are electrically stable at high temperatures. For example, planar bilayers made with bipolar lipids from a hyperthermophile, *Caldariella acidophila*, are stable at up to 80° C.[5] The studies described herein were carried out with planar bilayers made from 1,2-diphytanoyl-sn-glycero-3 phosphocholine (DPhPC), which exist as a single phase at up to 120° C. as determined by NMR and X-ray diffraction.[17] In the studies described herein, the bilayers remained stable at 98° C. as determined by capacitance measurements (FIG. 5A). The saturated isoprenoid side-chains of DPhPC resemble those found in certain thermophiles,[18] which may contribute to the stability of the bilayers. Multichannel current recordings in response to a temperature ramp were carried out on WT (wild-type) αHL pores incorporated as preformed heptamers into DPhPC bilayers from the cis chamber.

Figure 4:
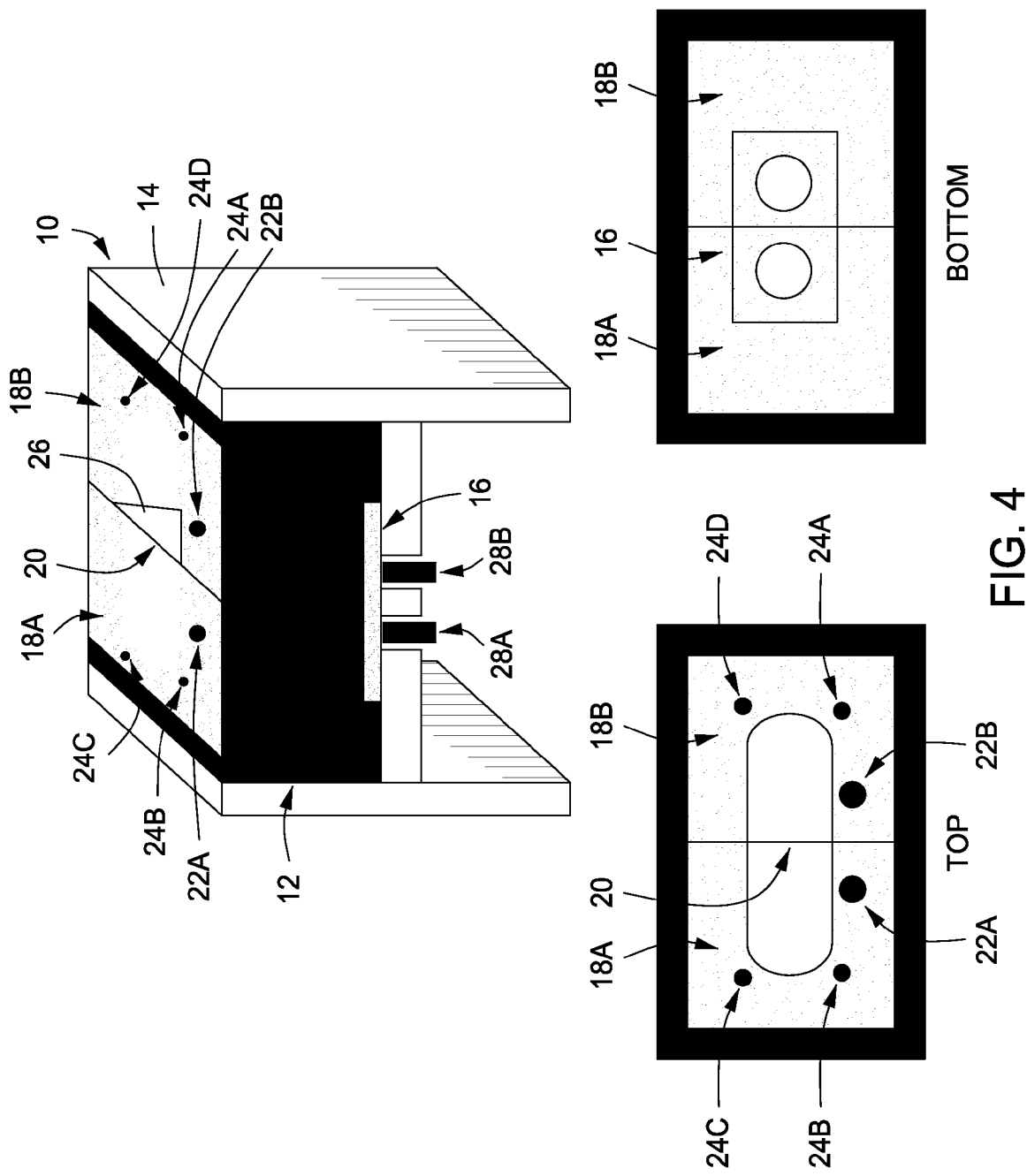
FIG. 4 illustrates one embodiment of the apparatus of the present invention.
Figure 5B:
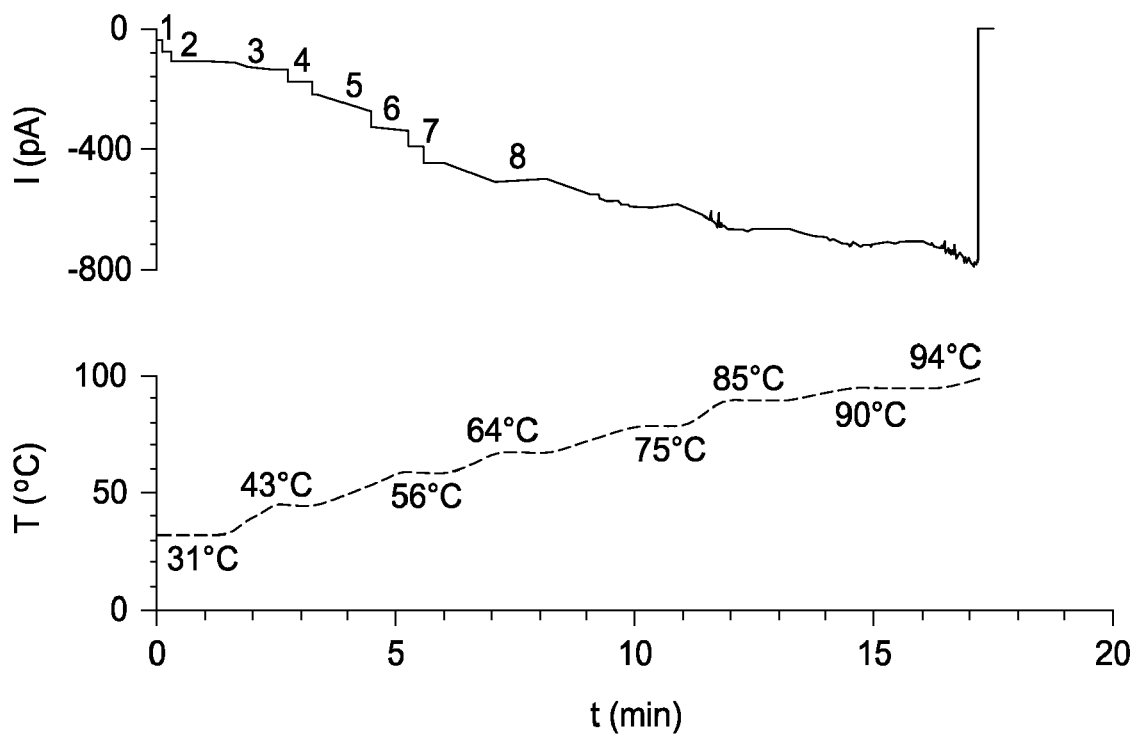

In all the studies conducted herein, both chambers of the measurement device (FIG. 4) contained 1 M NaCl with 10 mM Na phosphate, pH 7.5, and unless otherwise noted recordings were made at −40 mV. The αHL pores were stable at up to 94° C. (FIG. 5B). WT-αHL pores had been shown to be stable in SDS at up to ~65° C., as judged by SDS polyacrylamide gel electrophoresis.[19,20] This stability and functionality at higher temperatures has not previously been demonstrates, nor was it expected based upon earlier studies. It is well known that most proteins experience increasing instability at higher temperatures. This decrease in stability correlates with a decrease in function that normally abrogates functionality at higher temperatures, or decreases it so severely that one would not expect the protein to be useful in any assay relying upon its function.

Figure 1B:
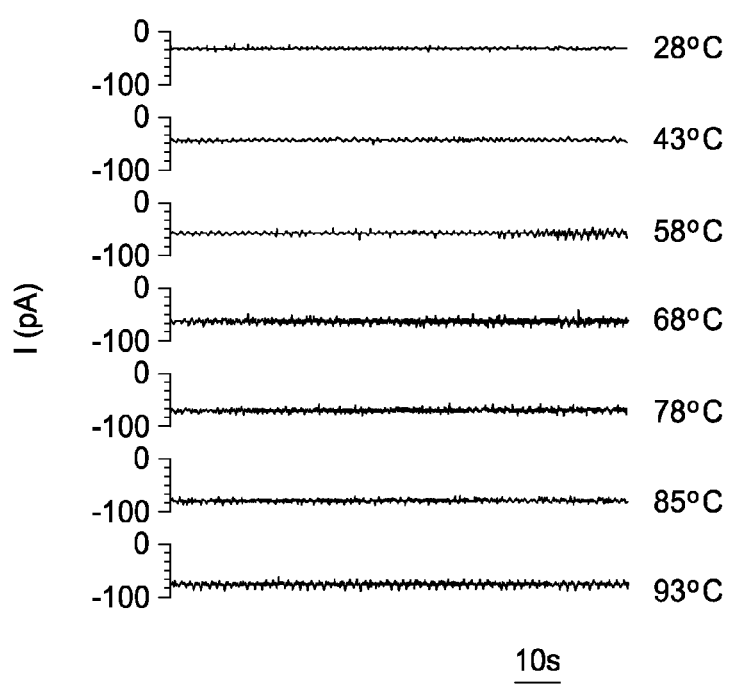
FIG. 1B are representative traces that illustrate single channel current traces of unoccupied WT-αHL pores at different temperatures.
Figure 1C:
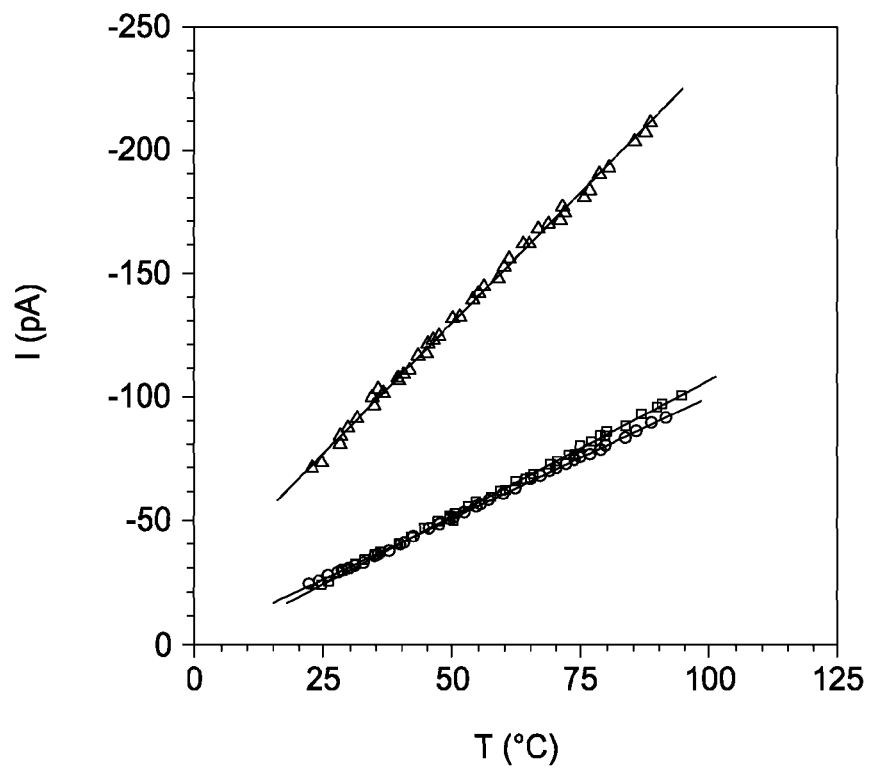
FIG. 1C is a graph that shows the variation of single channel currents with temperature for WT-αHL (○), Luk (Δ) and OmpG (□) pores. The values from four different experiments are compiled in each plot. The single channel currents depended linearly on the temperature: WT αHL, $I(pA)=4.18+0.944T(°C.)$ $(R=0.999)$; Luk, $I(pA)=26.4+2.04T(°C.)$ $(R=0.999)$; OmpG, $I(pA)=0.373+1.05T(°C.)$ $(R=0.999)$.
Figure 1D:
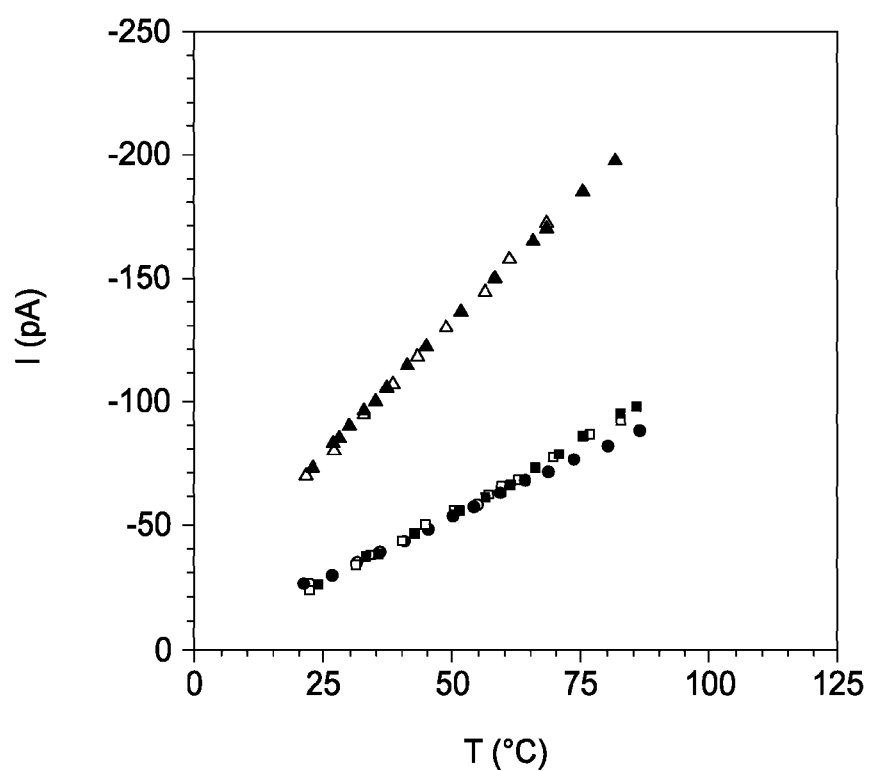
FIG. 1D is a graph that shows that changes in single-channel currents are reversible: WT-αHL (○,●), Luk (Δ,▲) and OmpG (□,■) pores. The data are from single representative experiments. The unfilled symbols are data points obtained as the temperature was increased, the filled symbols are data points obtained as the temperature was subsequently decreased.

Single-channel current traces of WT-αHL pores were measured at up to 93° C. (FIG. 1B). The single-channel current increased roughly linearly from 26.4 pA at 22° C. to 91.9 pA at 93° C. In a similar manner, single-channel recordings were measured using the Luk and OmpG pores (FIG. 1C). Again, the currents increased roughly linearly with temperature: Luk, 72.0 pA at 23° C. to 210 pA at 90° C.; OmpG, 25.5 pA at 25° C. to 101 pA at 97° C. The highest temperatures recited are those that were reached before technical problems (such as the insertion of a second channel, which can occur at any temperature) were encountered or a reverse temperature ramp was intentionally initiated in the experiments being conducted at that time. However, the significance of the occurrence of these events on the functionality of the pores is not understood and in no way limits the present invention. Thus, the pores may well be stable and functional at yet higher temperatures. The occurrence of numerous spikes towards zero current distinguished the OmpG traces from those arising from the αHL pore, which has a similar conductance, thereby ruling out sample contamination. The stabilities of the Luk and OmpG pores were surprising based on their established properties in detergent solutions; Luk pores dissociate in SDS at -78° C. (L. Jayasinghe, personal communication) and the OmpG protein unfolds in n-octyl-β-0-glucopyranoside at 63° C.[11] The changes in single-channel current associated with the temperature ramp were fully reversible (FIG. 1D). Three main factors may contribute to the ability to record single channel currents at high temperatures (FIG. 4): (1) the use of an aperture with a diameter of ~100:m (with a larger orifice, multiple channels were incorporated too readily and the bilayer tended to break); (2) the formation of a bilayer by using a large mass of DPhPC (200:g lipid per chamber:electrolyte volume=1.5 mL, surface area=0.72 cm$^2$); and (3) the use of dilute protein samples.

Figure 1E:
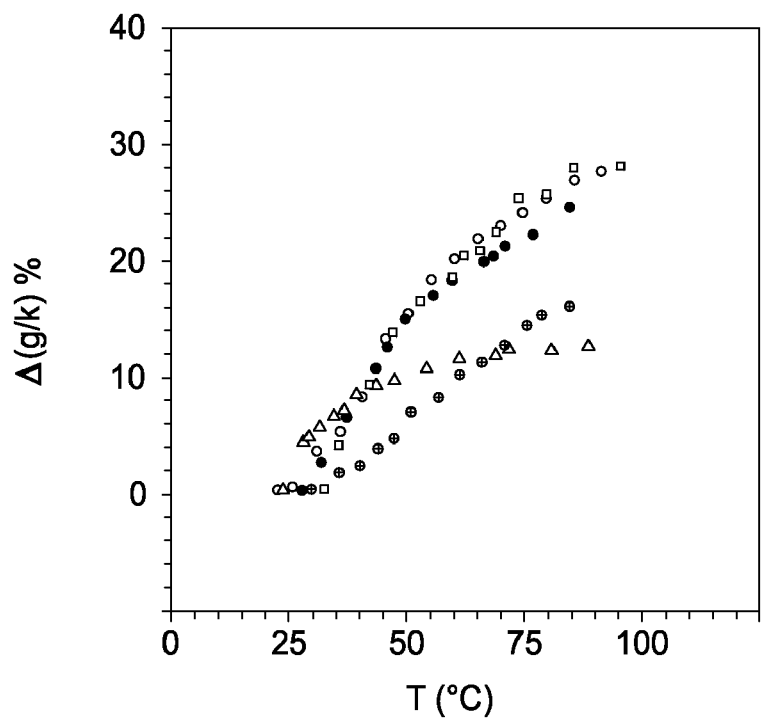
FIG. 1E is a graph that plots of the percentage change in g/κ as a function temperature for WT-αHL (○), αHL (M113N)$_7$ (●), αHL(M113N)$_7$·βCD (⊕), OmpG (□) and Luk (Δ) pores. The values at 23° C. were set to 0%. Values of g from FIG. 2 were used, with additional data for αHL (M113N)$_7$ and αHL (M113N)$_7$·βCD obtained under the same conditions. Values for solution conductivity, κ, were obtained from a linear fit to values of κ measured at different temperatures.

The strong temperature dependence of the single-channel conductance values (g) of the three pores is largely due to the variation of solution conductivity (κ) with temperature, which suggests that there is no appreciable molecular reorganization or subunit dissociation at elevated temperatures. The conductivity of the buffer was found to increase linearly with temperature from 20° C. to 90° C., κ=3.74+0.19T(° C.) S m$^{-1}$ (R=0.998, for all data points plotted from three experiments), which is closely similar to literature values for 1 M NaCl.[22] When g/κ was plotted as a function of temperature, the value increases slightly with temperature for all the pores examined (FIG. 1E). For the Luk pore, g/κ increased by ~13% over the 70° C. range. For WT-αHL, the mutant αHL M113.N and OmpG, the changes in g/K were larger at 26%, 25% and 24%, respectively. Because these relatively wide pores pass hydrated ions, the dominant effect of κ in determining g is reasonable.

It was found that the small change in g/κ with temperature was not due to a change in solution pH or the development of a small electrical potential in the apparatus (TABLES 1 and 2). Therefore, the most likely explanation derives from the mechanism of ion transport through the pores. While the pores in these studies transported hydrated ions, they are weakly ion selective. The selectivity derives from the interactions of the ions with the walls of the pore lumen. As the temperature increases, these interactions are weakened and the conductance of the pore increases to a greater extent than would be predicted from bulk conductivity measurements.

By comparison with the β barrels, the gating kinetics of several channels, including the temperature-gated vanilloid receptors, are characterized by dramatic responses to temperature (at below 55° C.).[23] Host molecules such as cyclodextrins can become lodged within the αHL pore, where they can in turn bind guest molecules (FIG. 1A).[24] Therefore, the interaction of β-cyclodextrin (βCD) with the (M113N)$_7$ pore at high temperatures was examined.

Figure 2:
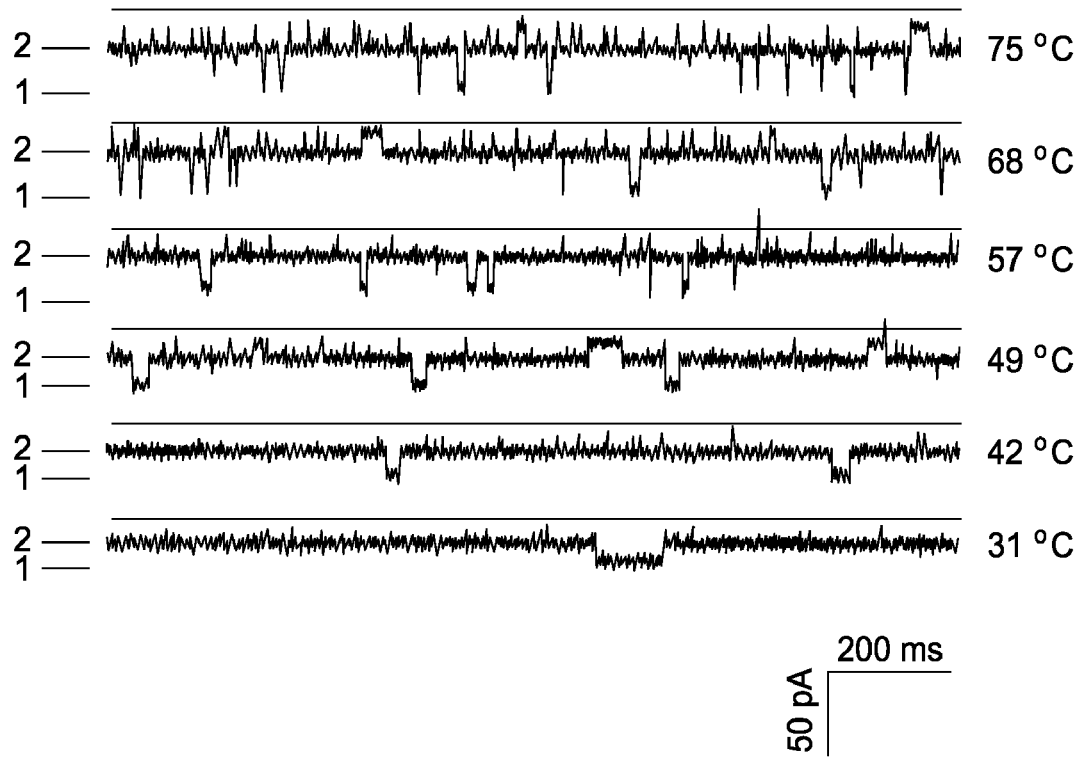
FIG. 2 includes representative traces that illustrate the interaction of βCD with αHL-(M113N)$_7$ pores obtained at various temperatures. Broken line, zero current; level 1, current through open (M113N)$_7$ pore; level 2, current through (M113N)$_7$·βCD. The conditions were as follows: the buffer in both chambers that was 10 mM Na phosphate, pH 7.5, containing 1 M NaCl and transmembrane potential was −40 mV.

At room temperature, the M113N mutant of αHL binds βCD>10,000-fold more tightly than the WT protein.[25] At 31° C., βCD binding events with a mean duration, $\tau_{off}$, of 14 s were seen (FIG. 2A). As the temperature increased, several phenomena were observed at a fixed βCD concentration: (1) the conductance values of both the unoccupied and occupied states of the pore increased; and (2) short additional blockades from the (M113N)$_7$·βCD level (sub states) were observed. The frequency of occurrence of these events was independent of βCD concentration, so they did not arise from the binding of a second βCD. Instead, they most likely represented as a second conformation of the occupied state, (M113N)$_7$·βCD. Specifically, they likely represented the rotation of βCD at the binding site or dewetting transitions[26] within the narrow cyclodextrin ring. Finally, the dwell time of βCD ($\tau_{off}$) and the intervals between the binding events ($\tau_{on}$) both decreased.

In earlier work at room temperature, it has been shown that βCD takes part in a simple binary interaction with (M113N)$_7$.[25] By a kinetic analysis, it was confirmed that this was also the case at 78° C. (FIG. S3). Measurements of the mean dwell time (τoff) and the mean inter-event interval ($\tau_{on}$) were used to derive association ($k_{on}$) and dissociation ($k_{off}$) rate constants for βCD. At 25° C., the values were 4.5±0.6× 10$^5$ M$^{-1}$s$^{-1}$ and 0.031±0.01 s$^{-1}$ (n=3) respectively, yielding $K_f$=1.5×10$^7$ M$^{-1}$ (literature 7.7×10$^6$ M$^{-1}$, the latter value was determined in a different sequence background for αHL, "RL2", which might explain the small difference[25]). This value is >10$^4$-fold greater than the value for the interaction of WT-αHL with βCD (290 M$^{-1}$) reported previously.[25] As the temperature increased, $k_{on}$ and $k_{off}$ increased. For example at 85° C., the highest temperature reached in these experiments, $k_{on}$ and $k_{off}$ increased by ~15-fold and ~800-fold to 6.5±0.8× 10$^6$ M$^{-1}$ s$^{-1}$ and 25.0±0.3 S$^{-1}$ (n=3), respectively, over the values at 25° C. Because there is a larger increase in $k_{off}$ with temperature, compared with $k_{on}$, the formation constant $K_f$ was reduced to 2.6×10$_5$ M$^{-1}$ at 85° C.

Figure 7A:
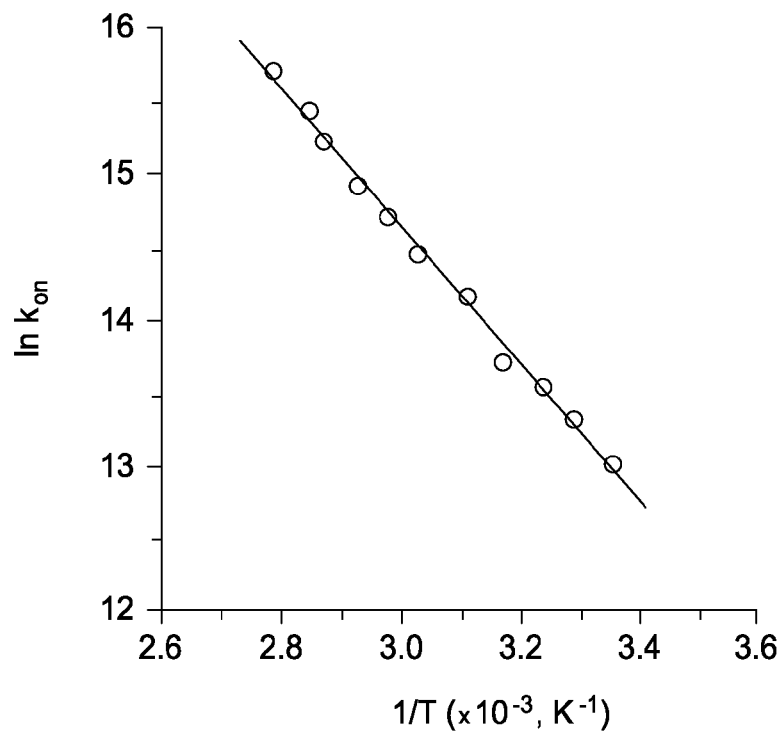
FIGS. 7A to 7C shows the interaction of βCD with αHL-(M113N)$_7$ pores. The conditions were as described in FIG. 2. Kinetic constants were derived as described herein.
Figure 7B:
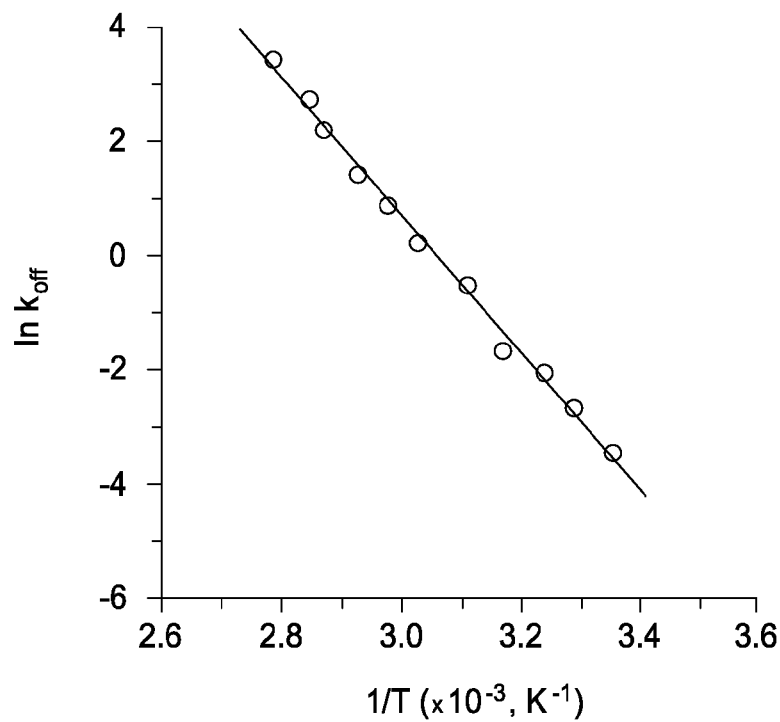
Figure 7C:
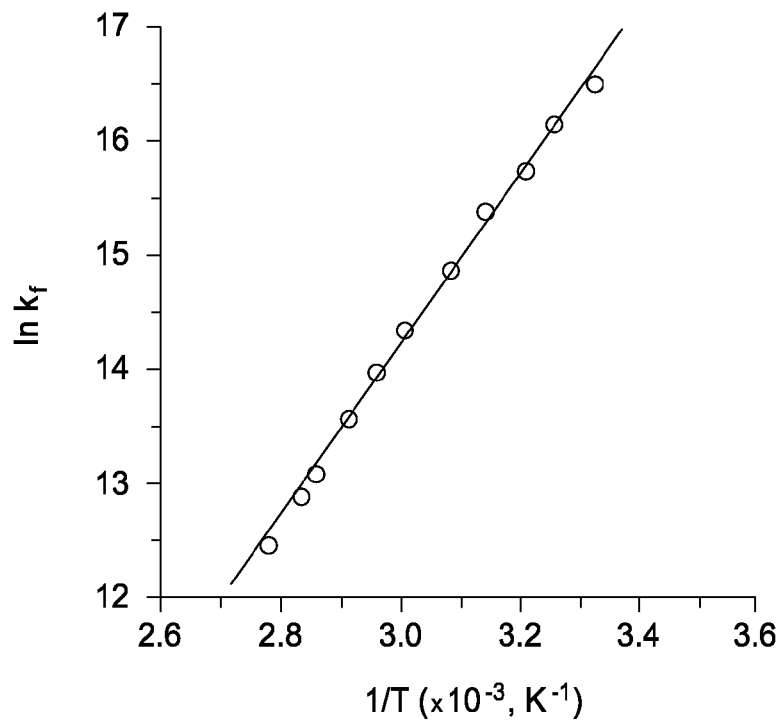
Figure 8B:
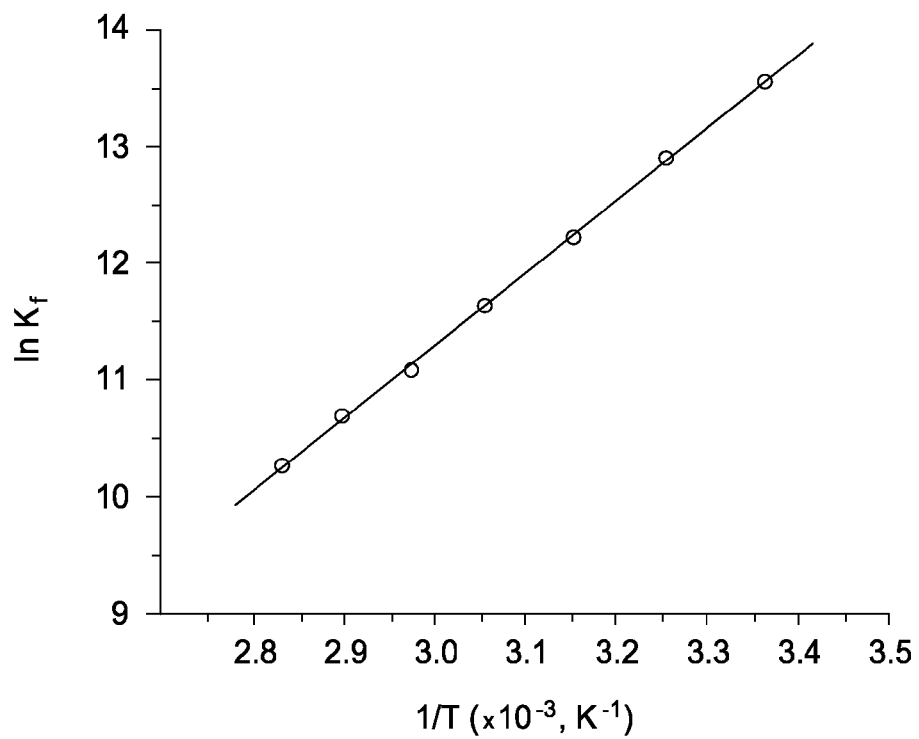
FIGS. 8A and 8B illustrate the interaction of βCD with WT$_1$(M113N)$_6$ pores.
Figure 8A:
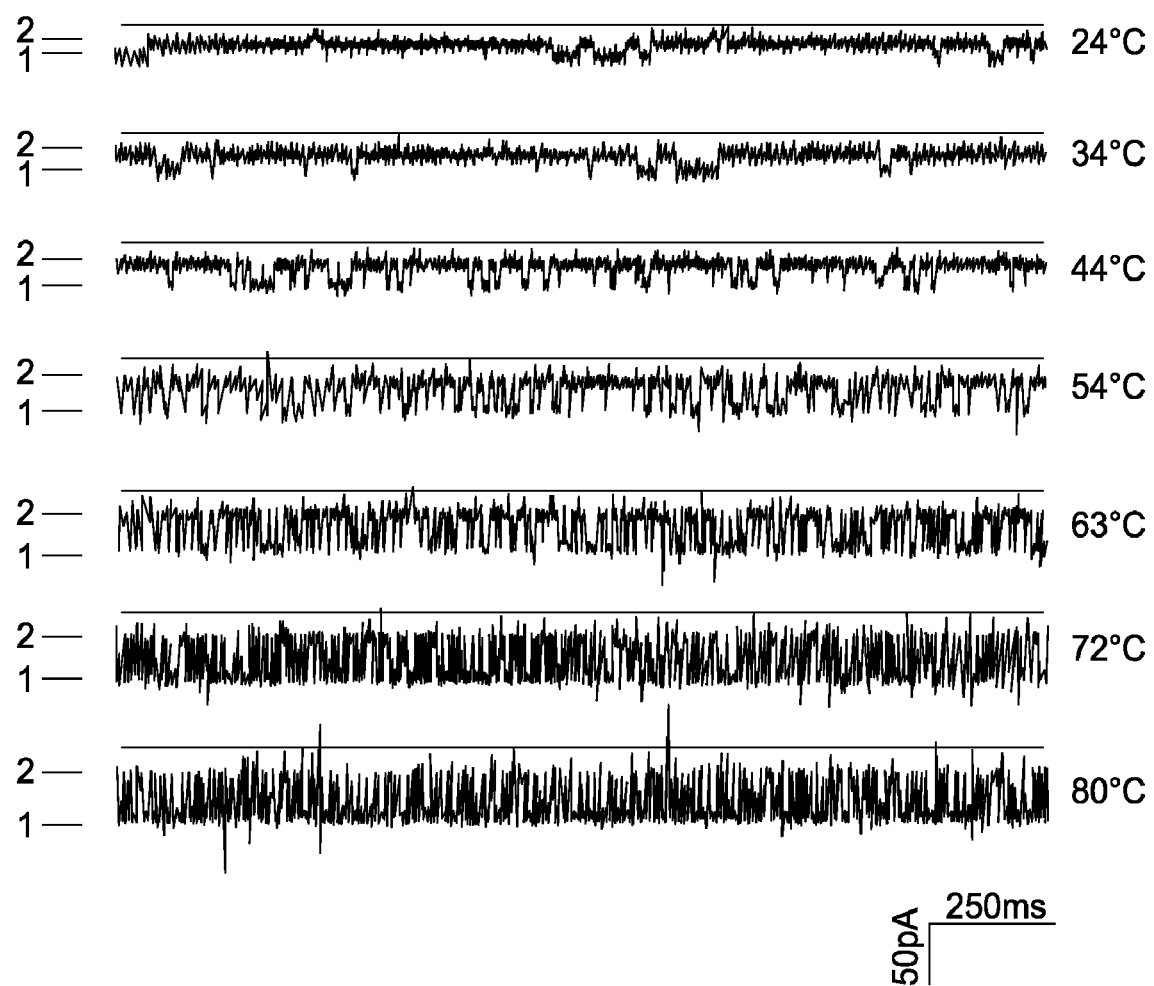

From the slope of a linear fit to ln $K_f$ versus 1/T (FIG. 7C), ΔH° and ΔS° values were found to be, respectively, -60±4 kJ mol$^{-1}$ and -62±5 J mol$^{-1}$ K$^{-1}$, yielding a value of ΔG°=-41±3 kJ mol$^{-1}$ at 25° C. (n=4). The value for ΔH° is close to that for the binding of βCD to glucoamylase, while the value for ΔS° for glucoamylase is a less favorable -90 J mol$^{-1}$ K$^{-1}$,[27-29] suggesting a more favorable preorganization of the binding site in (M113N)$_7$, which would be augmented by the matching C$_7$ symmetry of the αHL pore and βCD. By comparison, for the formation of an 8-nucleotide DNA duplex under similar conditions[10]: ΔH°=-144 kJ mol$^{-1}$, ΔS°=-359 J mol$^{-1}$ K$^{-1}$, ΔG°=37 kJ mol$^{-1}$. In this case, a far larger entropic penalty is compensated for by a highly favorable enthalpic contribution. Binding experiments with βCD and the heteromeric[30,31] pore WT$_1$(M113N)$_6$ yielded ΔH°=-51±2 kJ mol$^{-1}$, ΔG°=-33±kJ mol$^{-1}$ K$^{-1}$, and ΔG°=-33±2 kJ mol$^{-1}$ at 25° C. (FIG. 8). The decrease in affinity brought about by the loss of one Asn-113 residue is almost entirely derived from a change in ΔH°, again suggesting a preorganized binding site.

$\Delta G^{\neq}$, $\Delta H^{\neq}$ and $\Delta S^{\neq}$ values for $\beta CD$ and $(M113N)_7$ were determined by using $\ln k\phi = -(\Delta H^{\neq}/R) \cdot 1/T + \Delta S^{\neq}/R$, where $\phi$ is a frequency factor in a simplified transition state theory that is useful for comparisons with related systems (FIGS. 7A and 7B).[32,33] For the dissociation of $\beta CD$, $\Delta H^{\neq}=99$ kJ mol$^{-1}$ and $\Delta S^{\neq}=130$ J mol$^{-1}$ K$^{-1}$, using $\phi=1$ ns$^{-1}$.[33] $\Delta G^{\neq}$ (25° C.)=60 kJ mol$^{-1}$=24RT; $\Delta G^{\neq}$ (85° C.)=53 kJ mol$^{-1}$=21RT. For the association of $\beta CD$, $\Delta H^{\neq}=39$ kJ mol$^{-1}$ and $\Delta S^{\neq}=66$ J mol$^{-1}$ K$^{-1}$, when $\phi=1$ ns$^{-1}$. $\Delta G^{\neq}$ (25° C.)=19 kJ mol$^{-1}$ and $\Delta S^{\neq}=66$ mol$^{-1}$ K$^{-1}$, when $\phi=1$ ns$^{-1}$. $\Delta G^{\neq}$ (25° C.)=19 kJ mol$^{-1}$=7.7RT; $\Delta G^{\neq}$ (85° C.)=15 kJ mol$^{-1}$=6.1RT. The value of $\Delta S^{\neq}=130$ J mol$^{-1}$ K$^{-1}$ for dissociation can be compared with the value of 310 J mol$^{-1}$ K$^{-1}$ ($\phi=1$ ns$^{-1}$) for the dissociation of the duplex formed by two complementary 8-mer DNAs.[10] In the latter case, the approach to the transition state must reflect a relatively large increase in disorder by comparison with that in $\beta CD$ dissociation.

Figure 3:
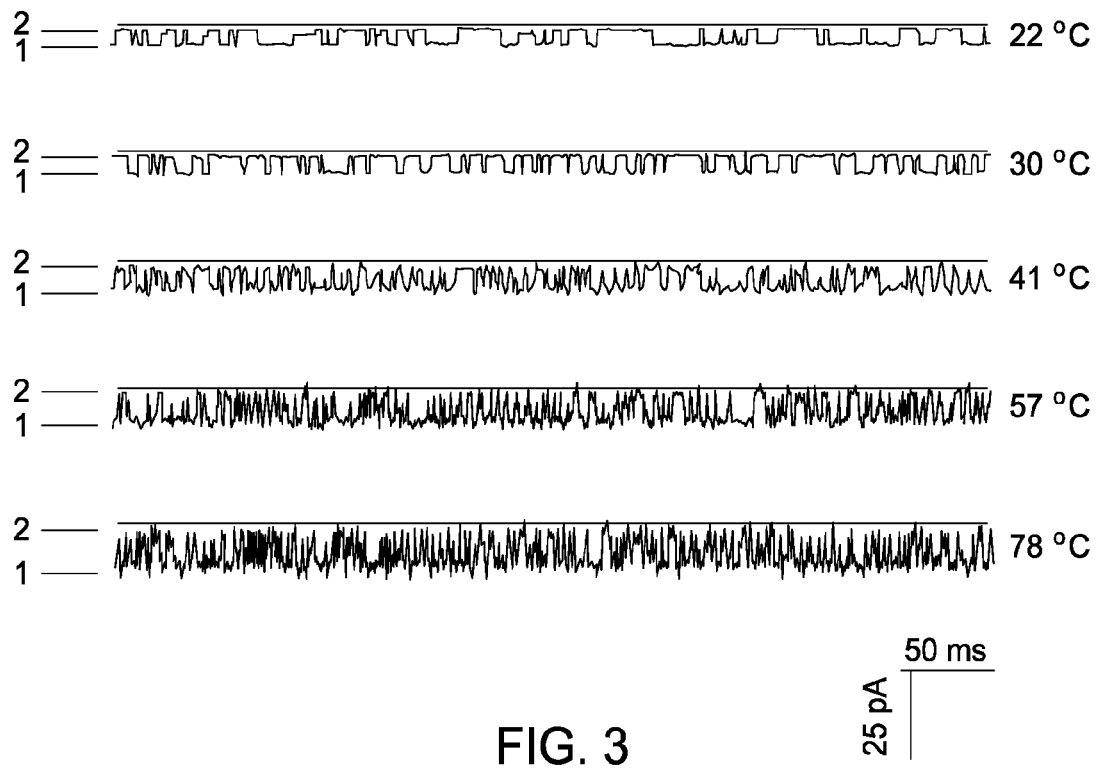
FIG. 3 includes traces that illustrate the interaction of the model analyte adamantane-1-carboxylic acid with βCD lodged in the αHL-(M113F/K147N)7 pore. Representative traces show the interaction of αHL-(M113F/K147N)$_7$·βCD with adamantane-1-carboxylic acid at various temperatures. βCD (40 μM) was applied to the cis side of the bilayer; adamantane-1 carboxylic acid (20 μM) was applied to the trans side. Otherwise, the conditions were as follows: the buffer in both chambers that was 10 mM Na phosphate, pH 7.5, containing 1 M NaCl, except that the applied transmembrane potential was −60 mV. Broken line, zero current; level 1, αHL-(M113F/K147N)$_7$·βCD; level 2, αHL-(M113F/K147N)$_7$·βCD blocked with adamantane-1-carboxylic acid.

$\beta CD$ is a host for a wide variety of guest molecules.[34] Therefore, the $\alpha HL$ pore equipped with $\beta CD$ as a molecular adapter can act as a sensor element for the stochastic detection of small organic molecules.[24] The system of the present invention functions at elevated temperatures by using adamantane-1-carboxylic acid as a model analyte.[24] Although the $(M113N)_7$ pore binds $\beta CD$ at high temperatures, the appearance of substates (partial closures during occupancy by $\beta CD$, FIG. 2A), which are dependent on both temperature and the applied potential, limits its use in stochastic detection. Accordingly, a homoheptameric pore made from the double mutant M113F/K147N was used, which has the following characteristics (unpublished work): (1) there are no sub states during occupancy by $\beta CD$; (2) the binding affinity for $\beta CD$ is high: $K_f$(trans)=1.3±0.2×10$^5$ M$^{-1}$ (n=4) at −40 mV, cf. $\alpha HL$-WT$_7$,[25] $K_f$(trans)=3.0×10$^2$ M$^{-1}$; and (3) $\beta CD$ binds from both the cis and trans side of the bilayer. In $\alpha HL$-WT$_7$ and most other mutants, $\beta CD$ binds only from the trans side. $\beta CD$ (cis) bound to $(M113F/K147N)_7$ for extended periods ($\tau_{off}=7.0±0.3$ s, n=3, at −60 mV), during which an interaction with adamantane-1-carboxylic acid (trans) was observed (FIG. 3A). At 22° C. and 65° C. it was determined that the mean residence time ($\tau_{off}$) of the analyte was independent of analyte concentration and that $1/\tau_{on}$ ($\tau_{on}$, the inter-event interval) was linearly dependent on the analyte concentration. The independence of the analyte concentration is diagnostic of a bimolecular interaction between the analyte and $\beta CD$.[25,35]

Figure 9C:
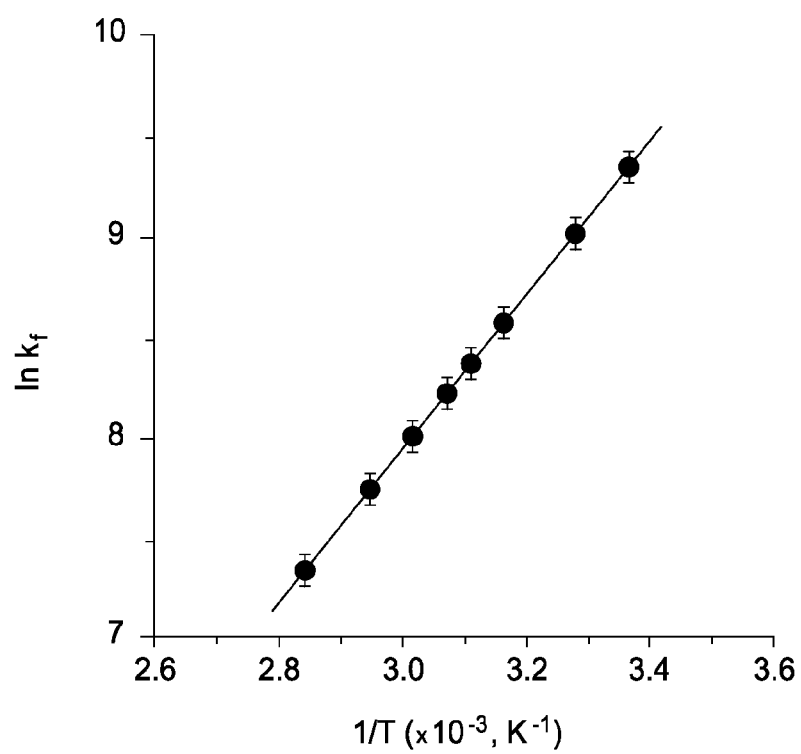
FIGS. 9A to 9C show the interaction of the model analyte adamantane-1-carboxylic acid with βCD lodged in the αHL-(M113F/K147N)$_7$ pore. βCD (40 μM) was applied to the cis side of the bilayer; adamantane-1-carboxylic acid (20 μM) was applied to the trans side. The conditions were as described in FIG. 3.
Figure 9A:
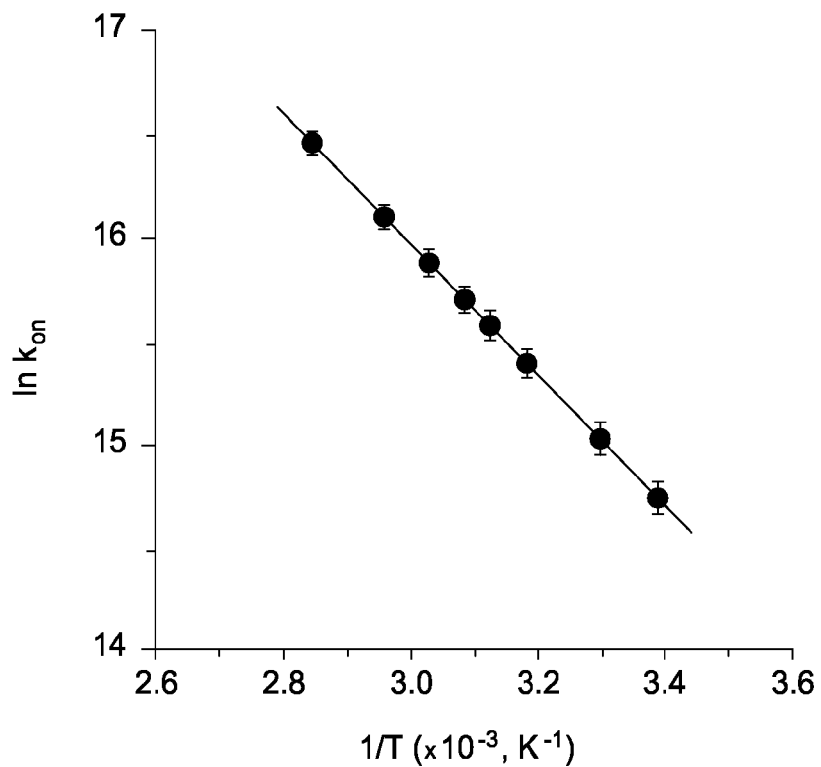
Figure 9B:
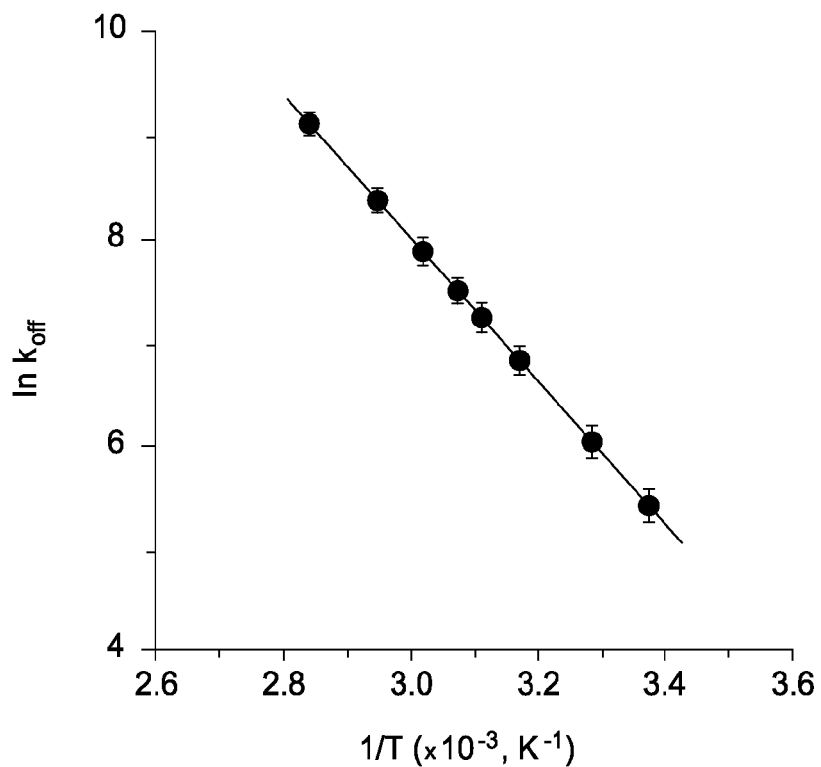

Kinetic constants were determined from $\tau_{on}$ and $\tau_{off}$ values. Over the temperature range 22° C. to 78° C., $k_{on}$ for adamantane-1-carboxylic acid increased by ~6-fold from 2.5±0.2× 10$^6$ M$^{-1}$ s$^{-1}$ (n=3) to 1.4±0.1×10$^7$ M$^{-1}$ s$^{-1}$ (n=3) and $k_{off}$ increased by ~43-fold from 2.1±0.2×10$^2$ s$^{-1}$ (n=3) to 9.3±0.6×10$^3$ s$^{-1}$ (n=3) (FIGS. 9A and 9B). The corresponding $K_f$ values ($K_f=k_{on}/k_{off}$), at 22° C. and 78° C., were respectively 1.2±0.1×10$^4$ M$^{-1}$ and 1.5±0.1×10$^3$ M$^{-1}$. From a plot of $\ln K_f$ versus 1/T (FIG. 9C), the $\Delta H°$ and $\Delta S°$ values of −31±2 kJ mol$^{-1}$ and −28±1 J mol$^{-1}$ K$^{-1}$ were obtained, yielding $\Delta G°=-23±2$ kJ mol$^{-1}$ at 25° C. (n=3). At least seven values for the standard thermodynamic constants are available in the literature[34] for adamantane-1-carboxylic acid as the carboxylate. They are in rough agreement with each other: $\Delta H°=-22$ kJ mol$^{-1}$, $\Delta S°=+10$ J mol$^{-1}$ K$^{-1}$, $\Delta G°=-25$ kJ mol$^{-1}$. While the value of $\Delta G°$ is close to that obtained here, $\Delta H°$ and $\Delta S°$ differ. Within the $\alpha HL$ pore, the enthalpy change for the interaction is less favorable, but a more favorable $T\Delta S°$ compensates. Perhaps the $\beta CD$ presents only one face to the guest presented from the trans side, or the $\beta CD$ is in a different conformation when lodged inside the pore than it is in solution. The binding site might also be better pre-organized than in solution, but offer less favorable non-covalent bonding interactions.

These studies show that the properties of protein pores may be examined at temperatures approaching 100° C. at the single-molecule level by planar bilayer recording. The approach developed herein may be useful in studies of the fundamental functional properties of ion channels, and of how they fold and assemble. All three pores examined herein contain transmembrane $\beta$ barrels, but the approaches described herein may also be applied to channels that are predominantly $\alpha$ helix. The pores examined are functional at high temperatures, although they originate in mesophilic bacteria. Pores from thermophiles may also be examined.[3] From the point of view of biotechnology, the ability to observe channels and pores at high temperatures aids in the ability to engineer stable membrane proteins[1] to act as components of devices such as sensors[36] or DNA sequencers.[37] Accordingly, aspects of the invention relate to an $\alpha HL$ pore containing a molecular adapter that retains its ability to bind a model analyte at elevated temperatures. Recently, the $\alpha HL$ pore has been used as a nanoreactor for the examination of single-molecule chemistry.[38-39] The ability to record at high temperatures greatly extends the power of this methodology.

It will be apparent to one skilled in the art that various alternative embodiments of the invention exist. For example, one may change the lipid used, incorporate alternative pores, vary the composition of the electrolyte, and change the material employed, nature of the electrode, dimensions, or other physical attributes of the testing apparatus.

The following examples are included to demonstrate specific embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention.

Example 1

Pore formation. Wild-type $\alpha HL$ pores were formed by treating monomeric $\alpha HL$, purified from *Staphylococcus aureus*, with deoxycholate (S. Bhakdi, R. Füssle, J. Tranum-Jensen, Proc. Natl. Acad. Sci. USA, 78, 5475-5479 (1981)). Heptamers were isolated from SDS-polyacrylamide gels (O. Braha, B. Walker, S. Cheley, J. J. Kasianowicz, L. Song, J. E. Gouaux, H. Bayley, Chem. Biol. 4, 497-505 (1997). The mutant $\alpha HL$ M113N, which was made in a WT-$\alpha HL$ background (L.-Q. Gu, S. Cheley, H. Bayley, Science 291, 636-640 (2001)), was synthesized in vitro by coupled transcription and translation (IVTT) and assembled into homoheptamers by the inclusion of rabbit red cell membranes (rRBCM) during synthesis (S. Cheley, O. Braha, X. Lu, S. Conlan, H. Bayley, Protein Sci. 8, 1257-1267 (1999)). The heptamers were purified by SDS-polyacrylamide gel electrophoresis and stored in aliquots at −80° C. Leukocidin pores were prepared by co-translation of the F and S subunits in the presence of rRBCM and purified by electrophoresis (G. Miles, S. Cheley, O. Braha, H. Bayley, Biochemistry 40, 8514-8522 (2001)). Stock solutions of the $\alpha HL$ and Luk pores were ~200 ng mL$^{-1}$. They were diluted 10- to 20-fold with 10 mM Na phosphate, pH 7.4, containing 1 M NaCl, and 0.5 to 1.0 µL was added to the cis chamber of the bilayer apparatus (1.5 mL). The porin Omp G was prepared and purified as described previously (S. Conlan, Y. Zhang, S. Cheley, H. Bayley, Biochemistry 39, 11845-11854 (2000)). The stock solution (0.56 mg mL$^{-1}$) in 10 mM Tris.HCl, pH 8.0, containing 150 mM NaCl and 1% (w/v) Genapol X-080 was diluted 5-fold with 10 mM Na phosphate, pH 7.4, containing 1 M NaCl, and 1.0 μL was added to the cis chamber (1.5 mL).

Example 2

Apparatus. One example of the detector 10 used in conjunction with the studies described herein includes a specially designed Teflon block 12, a stainless steel stand 14, and a Peltier device 16 (FIG. 4, side, top and bottom views). The block 12 includes two chambers (18A, 18B), designated cis and trans (or alternatively, first and second shambers). The planar lipid bilayer is formed across a 100-150 μm-diameter orifice in a 25 μm thick Teflon film 20 that separates the two chambers 18A, 18B. The bigger cylindrical holes (22A, 22B) (diameter=5 mm), which are connected to the main chambers 18A, 18B, are used for holding the electrodes (not depicted). The smaller holes (24A-D) (diameter=1.5 mm) are used for holding a thermocouple (not depicted), the tip of which is exposed to an electrolyte and therefore accurately monitors the temperature in the main chamber. The two chambers 18A, 18B are clamped tightly together in a stand 14 made of, e.g., stainless steel. The bottoms of the chambers 18A, 18B were covered with a single thin sheet of borosilicate glass 26 (0.16 mm thick) for efficient heat transfer between the solution in the chambers 18A, 18B and the surface of the Peltier device 16. The Peltier device 16 and the chambers 18A, 18B are mounted on a stainless steel stand 14, which provides efficient heat dissipation during cooling. The temperature in the chamber 12 was controlled by varying the current through the Peltier device 16 with a DC power supply (not depicted). The apparatus 10 may also include one or more stirring motors (28A, 28B).

Example 3

Temperature Control. The temperature in the chamber 12 (FIG. 4) was controlled by using a Peltier device 16 (Ferro-Tec, TZ21084-01). The top part of the chamber was built from Teflon, but the bottom was formed from a thin piece of borosilicate glass 26 (0.16 mm thick; Lab-Tek, Part No. 155361), so that heat transfer between the solution in the chamber 12 and the surface of the Peltier device 16 element was efficient. The temperature in the chamber 12 was controlled by varying the current through the Peltier device 16 with a DC power supply (TENMA, 72-6153). To reverse the temperature ramp, the polarity of the DC power was switched. Cooling was aided by the steel stand 14 underlying the glass bottom. The temperature of the electrolyte in the chamber 12 was recorded with a calibrated thermocouple. The system rapidly and accurately controls the solution temperature: heating rate 35° C. $min^{-1}$; cooling rate 10° C. $min^{-1}$; temperature: ±0.2°e. It can be used over a broad temperature range, from room temperature to 100° C. The electrical noise is low (≦1.4 pA rms), similar to that found in room temperature recordings. In practice, steps of 5 to 10° C. were made (see e.g. FIG. 5); larger steps produced disturbances in the current recordings caused by bubble formation in the chambers. The temperature in the chambers was adjusted by manually varying the voltage of the DC power supply (this might readily be automated). Except for multichannel recordings (FIG. 5), continuous heating and recording was not used because the absence of stirring led to interference by bubbles. During heating, and before recording, the solution was stirred. When the temperature of the solution stabilized at the desired value, the stirring was stopped and recording initiated.

Example 4

Planar Bilayer Recording. The buffer used for bilayer recording was 10 mM $Na_2HPO_4$/10 mM $NaH_2PO_4$, pH 7.5, containing 1M NaCl. Planar lipid bilayer membranes of 1,2-diphytanoyl-sn-glycero-3 phosphocholine (DPhPC) (Avanti Polar Lipids, Alabaster, Ala.) were formed by the method of Montal and Mueller (M. Montal, P. Mueller, Proc. Natl. Acad. Sci. U5A 69, 3561-3566 (1972)) on a 100- to 150-μm diameter orifice in a 25-μm thick Teflon film (Goodfellow Corp., Malvern, Pa.) separating the cis and trans compartments (each 1.5 mL) of a Teflon apparatus. Prior to formation of the bilayer, the orifice was pretreated with a 1:10 hexadecane/pentane mixture. The level of the buffer in each chamber was set just below the aperture and 1% (w/v) DPhPC in pentane (20 μL) was transferred to each chamber and allowed to spread on the surface of the buffer. After 3 min, during which the pentane evaporated, the buffer level in each chamber was raised above the aperture. The formation of a bilayer was monitored by observing the increase in membrane capacitance to a value of approximately 8-10 μfF $μm^{-2}$. Larger orifices and the application of less lipid tended to give less stable bilayers at elevated temperatures.

All proteins were added to the cis chamber, which was held at, e.g., ground. A positive potential indicates a higher potential in the trans chamber, and a positive current is one in which cations flow from the trans to the cis side. With respect to the αHL pore, this convention means that the cap domain (L. Song, M. R. Hobaugh, C. Shustak, S. Cheley, H. Bayley, J. E. Gouaux, Science 274, 1859-1865 (1996)) is exposed to the cis chamber, while the entrance to the transmembrane β barrel at the tip of the stem domain is exposed to the trans chamber. A potential difference was applied across the bilayer with two freshly prepared Ag/AgCl electrodes in 1.5% agarose (Bio-Rad) saturated with 3 M KCl. Before each experiment, the two electrode potentials were carefully checked against a standard calomel electrode to ensure that the potential difference between them was <1.5 mV. Currents were recorded at a holding potential of −40 mV by using a patch clamp amplifier (Axopatch 200B, Axon Instruments). The signal was low-pass filtered with a built-in four-pole Bessel filter set at 5 kHz and sampled at 20 kHz by computer with a Digidata 1200 A/D converter (Axon Instruments). β-Cyclodextrin (Aldrich) was added to the trans chamber, except in the case of the αHL-$(M113F/K147N)_7$ pore when it was added to the cis chamber.

Example 5

Data analysis. Data were analyzed and presented by using the software pClamp 7.0 (Axon Instruments) and Origin 5.0 (Microcal, Northampton, Mass.). Conductance values were obtained from the peaks of all-point histograms. To determine kinetic constants for the binding of βCD to the αHL pore, $τ_{on}$ (the interevent interval) and $τ_{off}$ (the lifetime of the αHL·βCD complex) were obtained from dwell-time histograms fitted to single exponentials by the Levenberg-Marquardt procedure. To determine each set of kinetic constants, three or more experiments were performed. In each case, data were analyzed that had been acquired for at least 2 min. In all cases, the coefficient of determination of the fits was R≧0.85. Separate segments of the data yielded similar τ values, demonstrating that stationary kinetics prevailed. Kinetic constants were calculated by using $k_{off}=1/τ_{off}$, $k_{on}=1/τ_{on}[βCD])$, and $K_f=k_{on}/k_{off}$, where [βCD] is the concentration of βCD. Standard thermodynamic values, ΔG°, ΔH° and ΔS°, were determined by using $ΔG°=ΔH°−TΔS°=−RT \ln K_f$ and $\ln K_f=−(ΔH°/R)·1/T+ΔS°/R$. $ΔG^≠$, $ΔH^≠$ and $ΔS^≠$ were determined by using $\ln kφ=−(ΔH^≠/R)·1/T+ΔS^≠/R$, where φ is a frequency factor in transition state theory. The kinetics of the interaction of adamantane-1-carboxylic acid with βCD lodged in the αHL-(M113F/K147N)$_7$ pore were examined in a similar way.

Example 6

Bilayer stability and macroscopic currents. Bilayer stability was determined by measuring the dependence of capacitance on temperature (FIG. 5A). Before single channel recordings were performed, preliminary experiments were conducted with multichannel currents at elevated temperatures (e.g. FIG. 5B). The displayed example of multichannel recording is typical. Additional pores became incorporated into the bilayer as the temperature increased. In the study shown, excess protein in the cis chamber was not washed out before the recording. However, washing did not prevent the incorporation of additional pores, which probably originated from protein that had adhered to the bilayer surface. Eventually, the bilayer shown contained about eight channels. At 94° C., the current dropped sharply to zero, indicating that either all eight channels closed simultaneously or that the entire bilayer had become occluded. At the same time the bilayer capacitance decreased from 120 pF to 50 pF, indicating an increase in thickness of unknown origin. All such recordings ended in this way.

Example 7

The effect of temperature on solution pH values. All measurements were carried out in 10 mM Na phosphate at pH 7.5 (titrated at 25° C.) containing 1 M NaCl. Phosphate buffer was chosen because of its low temperature coefficient: d(pH)/dT=−0.0013 pH deg$^{-1}$ in the range 25° C. to 50° C. and (pH)/dT=+0.0013 pH deg$^{-1}$ in the range 50° C. to 90° C. [R. G. Bates, J. Res. Natn. Bur. Stand., Phys. Chem. 66A (2), 179 (1962); R. P. Buck, S. Rondinini, A. K. Covington, F. G. K. Baucke, et al., Measurement of pH. Definition, standards and procedures. Pure Appl. Chem. 74, 2169-2200 (2002)]. In addition, the temperature coefficient was determined experimentally in the presence of 1 M NaCl by using a Ross® glass electrode (TABLE 1). The pH meter was calibrated at each temperature by using standard buffers. At or below 50° C., two-point calibration with standard buffers at pH 7.0 and pH 10.0 was used. Above 50° C., single-point calibration was used. The change in the glass electrode slope with temperature was automatically compensated with an ATC probe. Small changes in pH with temperature were observed and were in agreement with the values in the literature.

TABLE 1

| | Temp. | | | | | | | |
|---|---|---|---|---|---|---|---|---|
| | 25° C. | 30° C. | 40° C. | 50° C. | 60° C. | 70° C. | 80° C. | 90° C. |
| pH | 7.50 | 7.49 | 7.47 | 7.47 | 7.47 | 7.48 | 7.49 | 7.51 |

Example 8

The Effect of Temperature on the Electrode Potential. The cell in this example may be described as follows:

Ag|AgCl, NaCl (3.0M)||electrolyte solution NaCl (1.0 M)||NaCl (3.0 M), AgCl|Ag

Theoretical Calculations

The half-cell potential for a Ag/AgCl electrode can be written:

$$E_1 = E°_{Ag+} + RT_1/nF \ln(\alpha_{Ag+})$$

For the reaction, Ag$^+$+Cl$^-$=AgCl(s), $\alpha_{Ag+} \cdot \alpha_{Cl-}$=Ksp, where K$_{sp}$ is the solubility product for AgCl.

Therefore, for the first electrode:

$$E_1 = E°_{Ag+} + RT_1/nF \ln(Ksp/\alpha_{Cl-})$$

$$E_1 = E°_{Ag+} + RT_1/nF \ln(Ksp) = RT_1/nF \ln(\alpha_{Cl-})$$

Similarly, for the second electrode:

$$E_2 = E°_{Ag+} + RT_2/nF \ln(Ksp) - RT_2/nF \ln(\alpha_{Cl-})$$

In the chamber, the potential difference between the two electrodes is:

$$V = E_1 - E_2 + I \cdot R$$

where: I, current; R, resistance; V, applied potential.

For two matched Ag/AgCl electrodes at the same temperature and bathed in the same concentration of chloride ions:

$$E_1 = E_2 \text{ and } V = I \cdot R$$

$$E_1 = E°_{Ag+} + RT_1/nF \ln(Ksp_1/\alpha_{Cl-})$$

However, it is worth considering the effect of a small temperature differential. If it is assumed that there is a temperature difference ΔT=T$_2$−T$_1$ between the two electrodes:
Therefore, $$E_2 = E°_{Ag+} + RT_2/nF \ln(Ksp_2/\alpha_{Cl-})$$

$$\Delta E = E_1 - E_2 = R/nF \cdot [T_1 \ln(Ksp_1/a_{Cl-}) - T_2 \ln(Ksp_2/a_{Cl-})]$$

where R, Ksp$_1$, Ksp$_2$, and F are the gas constant (8.314 J mol$^{-1}$ K$^{-1}$), the solubility product of AgCl at T$_1$, the solubility product of AgCl at T$_2$, and the Faraday constant (96,500 C mole$^{-1}$) respectively.

When the temperatures are 26° C. at electrode 2 and 25° C. at electrode 1, ΔT=1° C., Ksp$_1$=1.85×10$^{-10}$ M2 at 25° C., Ksp$_2$=2.02×10$^{-10}$ M2 at 26° C. [Ksp$_1$ was obtained from "Solubilities of inorganic and organic compounds. Vol. 1: Binary systems, Part 1", H. Stephen, ed., Pergamon Press, Oxford; Ksp$_2$ was calculated by using ln (Ksp$_1$/Ksp$_2$)=(ΔH$_0$/R)(1/T$_1$−1/T$^2$), where ΔH$_0$ (65.6 kJ mol$^{-1}$) is the enthalpy of dissolution of AgCl [Y. Sun and Y. Xia, Anal. Chem. 74, 5279-5305 (2002)].

In 3 M NaCl solutions, there is:
ΔE=E$_1$−E$_2$=−0.24 mV, when electrode 2 is at the higher temperature.

In an applied potential of −40 mV, the current flowing through a single WT αHL pore at 25° C. in 10 mM Na phosphate at pH 7.5, containing 1 M NaCl, is −28 pA. So, the current shift ΔI caused by a potential change of −0.24 mV is −0.17 pA or 0.6% of the total current.

In the same way, ΔE and ΔI values can be estimated for different electrode temperature differences ΔT (TABLE 2).

TABLE 2

| ΔT (T-25, ° C.) | ΔE (mV) | ΔI (pA) |
|---|---|---|
| 1° C. | −0.24 | −0.17 |
| 2° C. | −0.54 | −0.38 |
| 3° C. | −0.78 | −0.55 |
| 4° C. | −1.05 | −0.74 |
| 5° C. | −1.24 | −0.87 |

Measurement of the potential difference between two Ag/AgCl electrodes at different temperatures. Measurements were carried out in 10 mM Na phosphate at pH 7.5 (titrated at 25° C.) containing 1 M NaCl. First, each Ag/AgCl electrode potential was examined at 25° C. in the cell: Ag|AgCl, NaCl (3.0 M)||10 mM Na phosphate (pH 7.5) NaCl (1.0 M)||SCE. The electrode potentials of two typical Ag/AgCl electrodes at 25° C. were −0.0201 V and −0.0186 V versus SCE: a difference of 1.5 mV. The same two Ag/AgCl electrodes were inserted into 10 mM Na phosphate buffer, pH 7.5, containing 1 M NaCl to determine the change in the potential difference between them with temperature (TABLE 3). As expected, no significant additional potential difference developed with increasing temperature. The largest measured potential difference for the two Ag/AgCl electrodes in the range 25° C. to 85° C. was 2.1 mV. The difference between this and the value at 25° C. is 0.6 mV, which with the WT-αHL pore would cause a current change of only 0.41 pA. It might be noted the temperature of the electrodes in the apparatus (FIG. 4) is probably somewhat lower than that of the electrolyte in the chambers.

TABLE 3

| temperature (° C.) | ΔE (mV) | ΔI (pA) |
|---|---|---|
| 25 | 1.50 | 1.02 |
| 35 | 1.62 | 1.10 |
| 45 | 1.97 | 1.34 |
| 55 | 1.56 | 1.06 |
| 65 | 2.10 | 1.43 |
| 75 | 1.71 | 1.16 |
| 85 | 1.78 | 1.21 |

Example 9

Figure 6A:
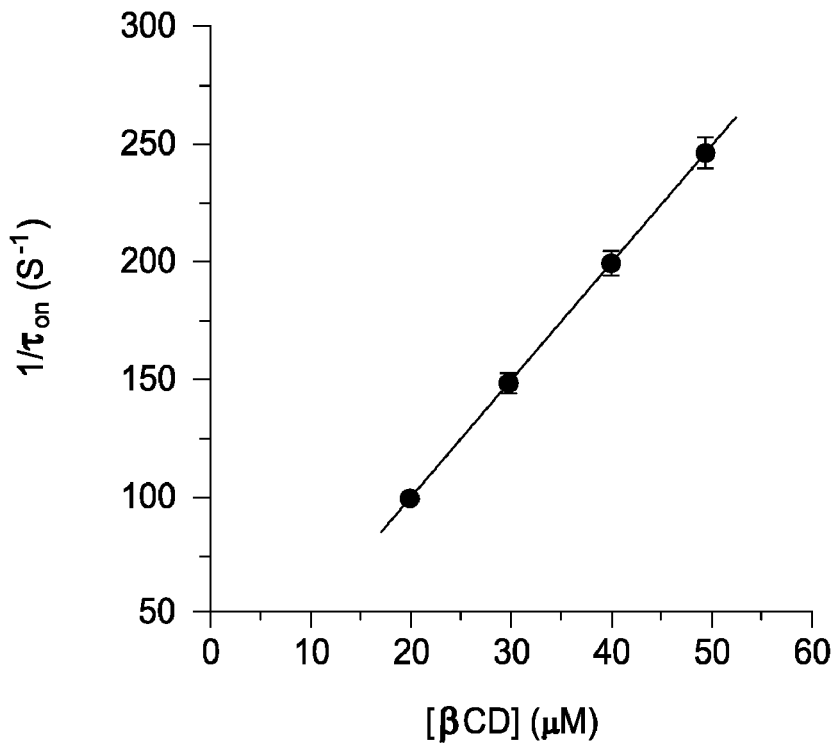
FIG. 6 is a graph that shows the dependence of $1/\tau_{on}$ (FIG. 6A) and $1/\tau_{off}$ (FIG. 6B) on the concentration of βCD (trans) for the αHL (M113N)$_7$ pore at 78° C.
Figure 6B:
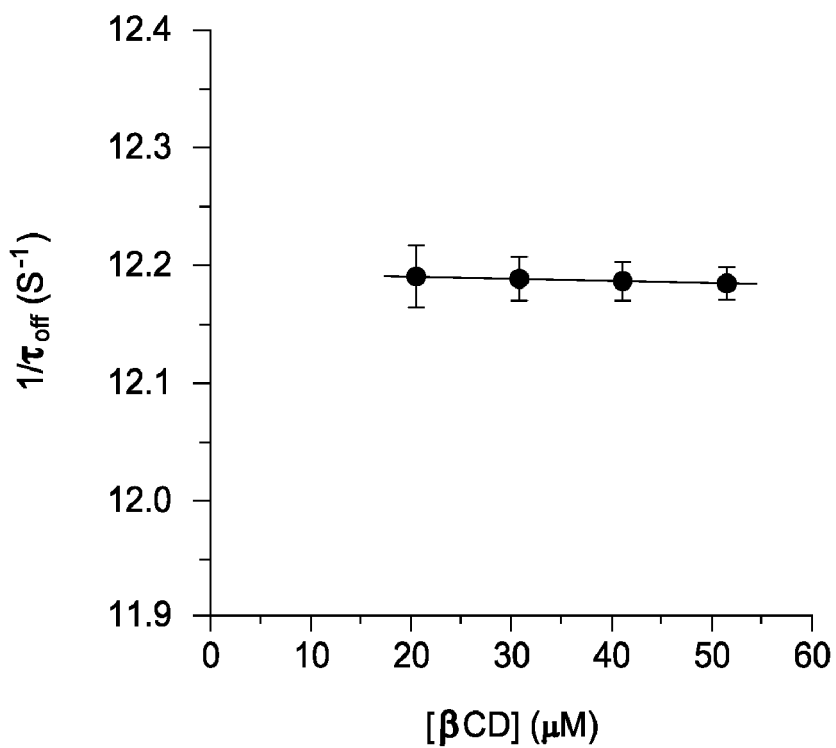

Binary interaction of βCD with the αHL (M113N)$_7$ pore at an elevated temperature. The existence of a binary interaction between βCD and the αHL (M113N)$_7$ pore was confirmed by examining the dependence of $1/\tau_{on}$ and $1/\tau_{off}$ on the concentration of βCD at 78° C. (FIG. 6).

Example 10

Temperature dependence of the interaction of βCD with αHL-(M113N)$_7$ pores. Kinetic constants were derived as described above and used to derive $\Delta G^{\neq}$, $\Delta H^{\neq}$ and $\Delta S^{\neq}$ and $\Delta G^0$, $\Delta H^0$ and $\Delta S^0$ values from ln k (or K) versus 1/T plots (FIG. 7).

Example 11

Interaction of βCD with a heteromeric αHL pore. The nature of the interaction of βCD with the αHL (M113N)$_7$ pore was further explored by examining the WT$_1$(M113N)$_6$ heteromer (FIG. 8).

Example 12

Temperature dependence of the interaction of the model analyte adamantane-1 carboxylic acid with βCD lodged in the αHL-(M113F/K147N)$_7$ pore. Kinetic constants were derived as described above and used to derive $\Delta G^{\neq}$, $\Delta H^{\neq}$ and $\Delta S^{\neq}$ and $\Delta G^0$, $\Delta H^0$ and $\Delta S^0$ values from ln k (or K) versus 1/T plots (FIG. 9).

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references are indicated by numeral throughout the specification.

[1] H. Bayley, L. Jayasinghe, *Mol. Membrane Biol.* 2004, 21, 209-220.
[2] T. Haltia, E. Freire, *Biochem. Biophys. Acta* 1995, 1241, 295-322.
[3] L. J. Rothschild, R. L. Mancinelli, *Nature* 2001, 409, 1092-1101.
[4] J. Wang, M. A. El-Sayed, *Biophys. J.* 2000, 78, 2031-2036.
[5] A. Gliozza, R. Rolandi, M. De Rosa, A. Gambacorta, *J. Membr. Biol.* 1983, 75, 45-56.
[6] M. J. Caterina, T. A. Rosen, M. Tominaga, A. J. Brake, D. Julius, *Nature* 1999, 398, 436-441.
[7] B. Liu, K. Hui, F. Qin, *Biophys. J.* 2003, 85, 2988-3006.
[8] G. Belmonte, L. Cescatti, B. Ferrari, T. Nicolussi, M. Ropele, G. Menestrina, *Eur. Biophys. J.* 1987, 14, 349-358.
[9] A. Meller, L. Nivon, E. Brandin, J. Golovchenko, D. Branton, *Proc. Natl. Acad. Sci. USA* 2000, 97, 1079-1084.
[10] S. Howorka, L. Movileanu, O. Braha, H. Bayley, *Proc. Natl. Acad. Sci. USA* 2001, 98, 12996-13001.
[11] S. Conlan, H. Bayley, *Biochemistry* 2003, 42, 9453-9465.
[12] L. Song, M. R. Hobaugh, C. Shustak, S. Cheley, H. Bayley, J. E. Gouaux, *Science* 1996, 274, 1859-1865.
[13] R. Olson, H. Nariya, K. Yokota, Y. Kamio, E. Gouaux, *Nature Struct. Biol.* 1999, 6, 134-140.
[14] J.-D. Pédelacq, L. Maveyraud, G. Prévost, L. Baba-Moussa, A. González, E. Courcelle, W. Shepard, H. Monteil, J.-P. Samama, L. Mourey, *Structure* 1999, 7, 277-288.
[15] G. Miles, L. Movileanu, H. Bayley, *Protein Sci.* 2002, 11, 894-902.
[16] G. Miles, S. Cheley, O. Braha, H. Bayley, *Biochemistry* 2001, 40, 8514-8522.
[17] H. Lindsey, N. O. Petersen, S. I. Chan, *Biochem. Biophys. Acta* 1979, 555, 147-167.

[18] V. Luzzati, A. Gambacorta, M. DeRosa, A. Gulik, *Ann. Rev. Biophys. Biophys. Chem.* 1987, 16, 25-47.
[19] A. C. McNiven, P. Owen, J. P. Arbuthnott, *J. Med. Microbiol.* 1972, 5, 113-122.
[20] B. Walker, H. Bayley, *Protein Eng.* 1995, 8, 491-495.
[21] S. Conlan, Y. Zhang, S. Cheley, H. Bayley, *Biochemistry* 2000, 39, 11845-11854.
[22] V. V. M. Lobo, J. L. Quaresma, *Handbook of Electrolyte Solutions. Part B*, Elsevier Science Publishers, New York, N.Y. 1989.
[23] M. Pusch, U. Ludewig, T. J. Jentsch, *J. Gen. Physiol.* 1997, 109, 105-116.
[24] L.-Q. Gu, O. Braha, S. Conlan, S. Cheley, H. Bayley, *Nature* 1999, 398, 686-690.
[25] L.-Q. Gu, S. Cheley, H. Baley, *J. Gen. Physiol.* 2001, 118, 481-494.
[26] O. Beckstein, M. S. P. Sansom, *Proc. Natl. Acad. Sci. USA* 2003, 100, 7063-7068.
[27] B. W. Sigurskjold, B. Svensson, G. Williamson, H. Driguez, *Eur. J. Biochem.* 1994, 225, 133-141.
[28] B. W. Sigurskjold, T. Christensen, N. Payre, S. Cottaz, H. Driguez, B. Svensson, *Biochemistry* 1998, 37, 10446-10452.
[29] J. Sauer, T. Christensen, T. P. Frandsen, E. Mirgorodskaya, K. A. McGuire, H. Driguez, P. Roepstorff, B. W. Sigurskjold, B. Svensson, *Biochemistry* 2001, 40, 9336-9346.
[30] O. Braha, B. Walker, S. Cheley, J. J. Kasianowicz, L. Song, J. E. Gouaux, H. Bayley, *Chem. Biol.* 1997, 4, 497-505.
[31] S. Howorka, S. Cheley, H. Bayley, *Nature Biotechnology* 2001, 19, 636-639.
[32] H. Gutfreund, *Kinetics for the Life Sciences*, Cambridge University Press, Cambridge, 1995.
[33] O. S. Andersen, *J. Gen. Physiol.* 1999, 114, 589-590.
[34] M. V. Rekharsky, Y. Inoue, *Chem. Rev.* 1998, 98, 1875-1917.
[35] E. Moczydlowski, in *Ion Channel Reconstitution* (ed. C. Miller), Plenum Press, New York, 1986, pp. 75-113.
[36] H. Bayley, P. S. Cremer, *Nature* 2001, 413, 226-230.
[37] D. W. Deamer, D. Branton, *Acc. Chem. Res.* 2002, 35, 817-825.
[38] S.-H. Shin, T. Luchian, S. Cheley O. Braha, H. Bayley, *Angew. Chem. Int. Ed.* 2002, 41, 3707-3709.
[39] T. Luchian, S.-H. Shin, H. Bayley, *Angew. Chem. Int. Ed.* 2003, 42, 1926-1929.
[40] T. Luchian, S.-H. Shin, H. Bayley, *Angew. Chem. Int. Ed.* 2003, 42, 3766-3771.

All references above and otherwise cited herein are incorporated by reference.

What is claimed is:

1. A method for sensing one or more analytes in a solution comprising:

disposing operably one or more protein pores in a divider between a first and a second chamber exposing said one or more protein pores to a solution suspected of comprising one or more analytes at a temperature at or above 55° C.; and detecting a current between the first and a second chambers with a current detector when the one or more protein pores are exposed to a solution suspected of comprising the one or more analytes at a temperature at or above 55° C., wherein each of the one or more protein pores comprise at least one high temperature stabilization molecular adapter that stabilizes the one or more protein pores at a temperature at or above 55° C. and the one or more analytes produces a change in current between the first and a second chambers detectable by the current detector.

2. The method of claim 1, wherein the one or more protein pores are engineered protein pores.

3. The method of claim 1, wherein one or more of the one or more protein pores is an αHL pore.

4. The method of claim 1, wherein the solution is a pH buffered KCl solution.

5. The method of claim 1, wherein the one or more analytes comprise an environmental toxin.

6. The method of claim 1, wherein the one or more analytes comprise a chemical weapon.

7. The method of claim 1, wherein the one or more analytes comprise a pharmaceutical.

8. The method of claim 1, wherein the one or more analytes comprise an arsenical.

9. The method of claim 1, wherein the solution comprises an ionic solution suspected of comprising one or more chemically distinct analytes capable of bonding with the one or more protein pores.

10. The method of claim 1, wherein the current detector is capable of stochastic sensing.

11. The method of claim 1, wherein the change in current comprises a change in the magnitude of the current.

12. The method of claim 1, wherein the at least one high temperature stabilization molecular adaptor comprises β-cyclodextrin (βCD).

* * * * *